United States Patent
Kim et al.

(10) Patent No.: US 11,951,204 B2
(45) Date of Patent: Apr. 9, 2024

(54) CELL-PENETRATING PEPTIDES AND COMPOSITION INCLUDING THE SAME

(71) Applicant: S-SKIN. CO., LTD., Yongin-si (KR)

(72) Inventors: Byung-Il Kim, Suwon-si (KR); Jeong Hee Im, Seongnam-si (KR); Jeong Gun Lee, Seoul (KR)

(73) Assignee: S-SKIN. CO., LTD., Yongin-si (KR)

( * ) Notice: Subject to any disclaimer, the term of this patent is extended or adjusted under 35 U.S.C. 154(b) by 0 days.

(21) Appl. No.: 17/935,593

(22) Filed: Sep. 27, 2022

(65) Prior Publication Data
US 2023/0248630 A1    Aug. 10, 2023

(30) Foreign Application Priority Data

Feb. 8, 2022    (KR) .......................... 10-2022-0016129

(51) Int. Cl.
| | |
|---|---|
| *C07K 7/06* | (2006.01) |
| *A61K 8/64* | (2006.01) |
| *A61K 47/64* | (2017.01) |
| *A61Q 19/00* | (2006.01) |

(52) U.S. Cl.
CPC ............... *A61K 8/64* (2013.01); *A61K 47/645* (2017.08); *A61Q 19/00* (2013.01); *C07K 7/06* (2013.01); *A61K 2800/10* (2013.01)

(58) Field of Classification Search
CPC ............. C07K 7/06; A61K 38/08; A61K 8/64
See application file for complete search history.

(56) References Cited

PUBLICATIONS

Kumar et al. "Peptides as skin penetration enhancers: Mechanisms of action", Journal of Controlled Release, 2015, 168-178 (Year: 2015).*
Wu et al. "Combination treatment with cyclosporin A and arsenic trioxide induce synergistic cell death via non-apoptotic pathway in uterine cervical cancer cells", Chemico-Biological Interaction, 2022 (Year: 2022).*
National Center for Biotechnology Information (2023). PubChem Compound Summary for CID 5284373, cyclosporin A. Retrieved Jun. 1, 2023 from https://pubchem.ncbi.nlm.nih.gov/compound/cyclosporin-A (Year: 2023).*
Hur et al. "Effect of oligoarginine conjugation on the antiwrinkle activity and transdermal delivery of GHL peptide", Journal of Peptide Science, 2020, 10 pages (Year: 2020).*
Zhang et al. "Polyarginine-Mediated siRNA Delivery: A Mechanistic Study of Intracellular Trafficking of PCL-R15/siRNA Nanoplexes", Mole. Pharmaceutics, 2020, 1685-1696 (Year: 2020).*
Hur et al. "Effect of oligoarginine conjugation on the antiwrinkle activity and transdermal delivery of GHK peptide", Journal of Peptide Science, 2020, 10 pages (Year: 2020).*
Talałaj et al. "The Effects of a Novel Series of KTTKS Analogues on Cytotoxicity and Proteolytic Activity", Molecules, 2019, 20 pages (Year: 2019).*
M. Green et al., Autonomous Functional Domains of Chemically Synthesized Human Immunodeficiency Virus Tat Trans-Activator Protein, Cell, vol. 55, 1179-1188, Dec. 23, 1988.
A. Joliot et al., Antennapediah omeoboxp eptider egulatesn eural morphogenesis, National Academy of Sciences of the United States of America, vol. 88, No. 5 (Mar. 1, 1991), pp. 1864-1868.

* cited by examiner

*Primary Examiner* — Lianko G Garyu
(74) *Attorney, Agent, or Firm* — Shih IP Law Group, PLLC.

(57) ABSTRACT

The present disclosure relates to a novel cell-penetrating multifunctional peptide, a composition including the same.

14 Claims, 58 Drawing Sheets

Specification includes a Sequence Listing.

FIG. 1A(ii)

FIG. 1A(iii)

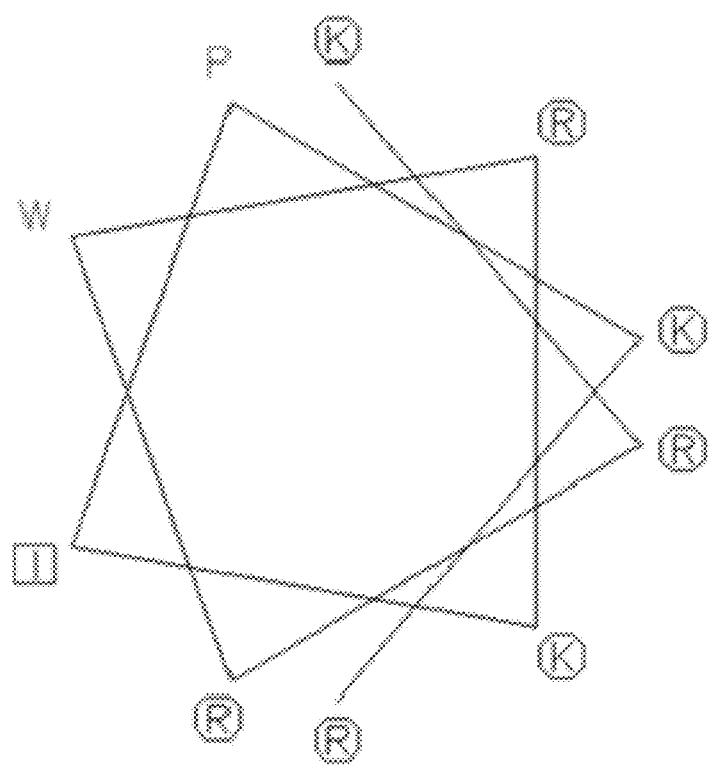
FIG. 1B(ii)

FIG. 1B(iii)
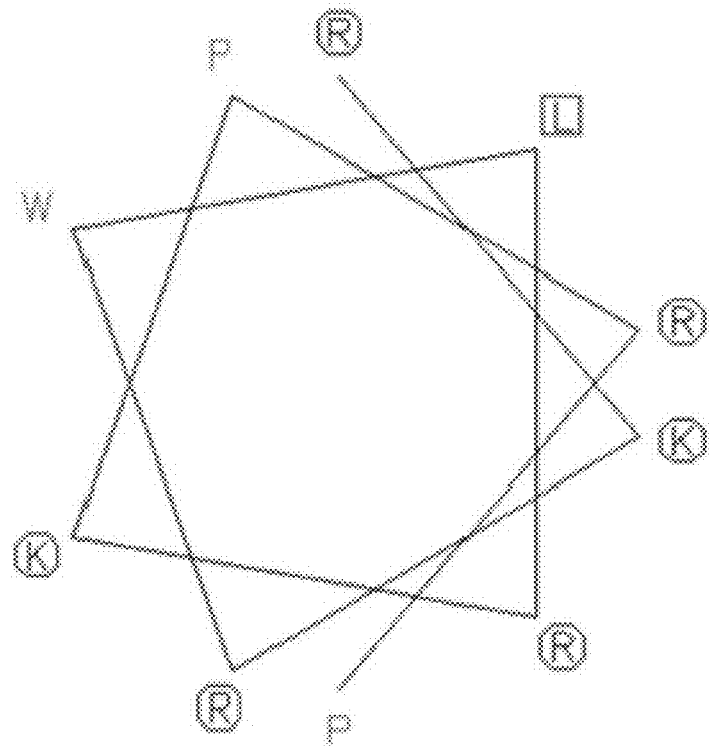
FIG. 2A(i)
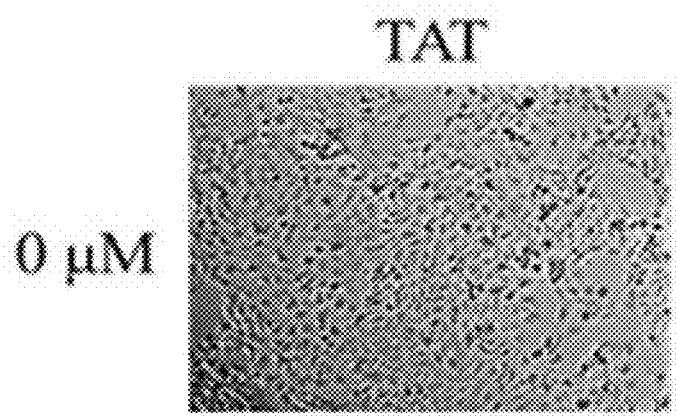

*FIG. 2A(ii)*
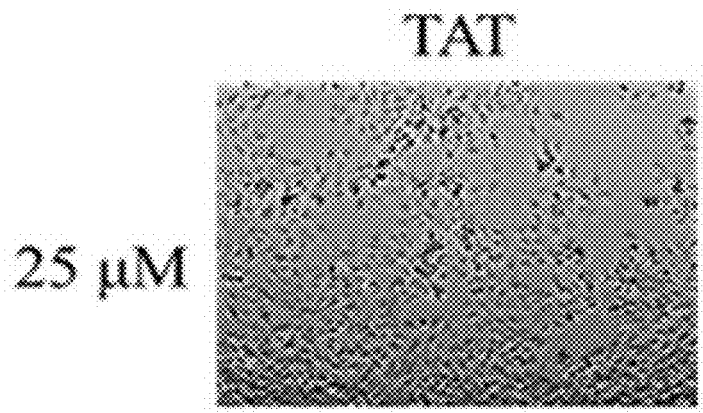
*FIG. 2A(iii)*
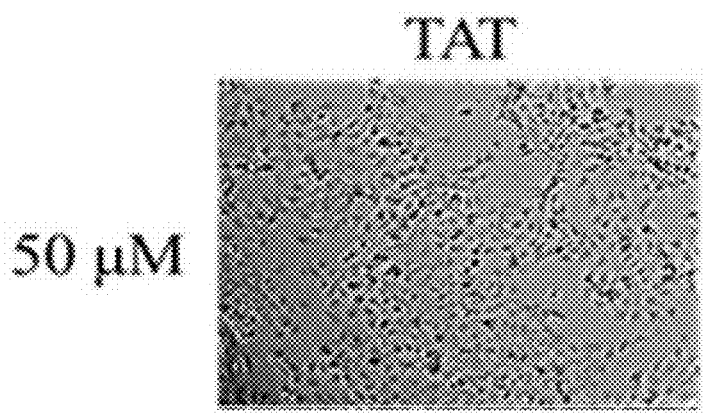
*FIG. 2A(iv)*
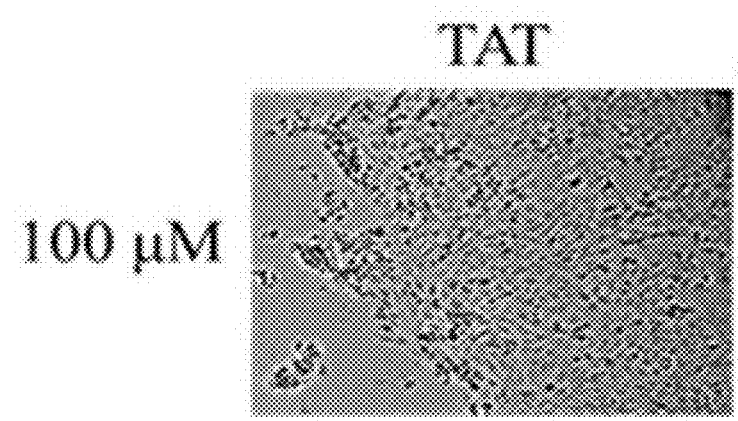

FIG. 2A(vi)

FIG. 2A(vii)

FIG. 2A(viii)
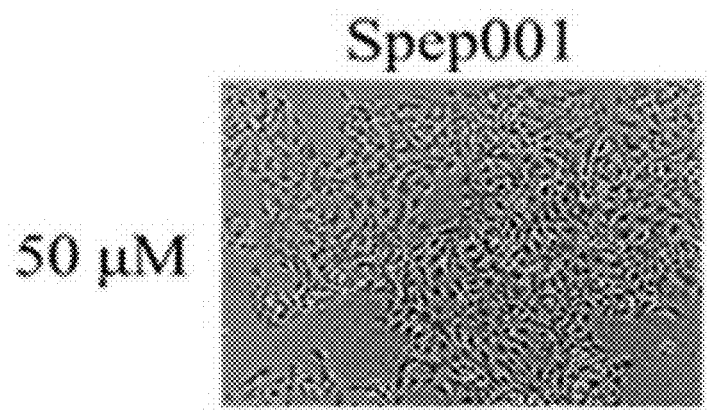
FIG. 2A(ix)
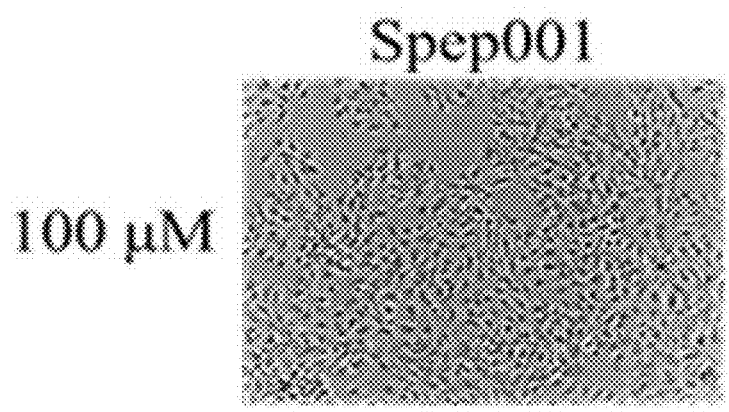
FIG. 2A(x)
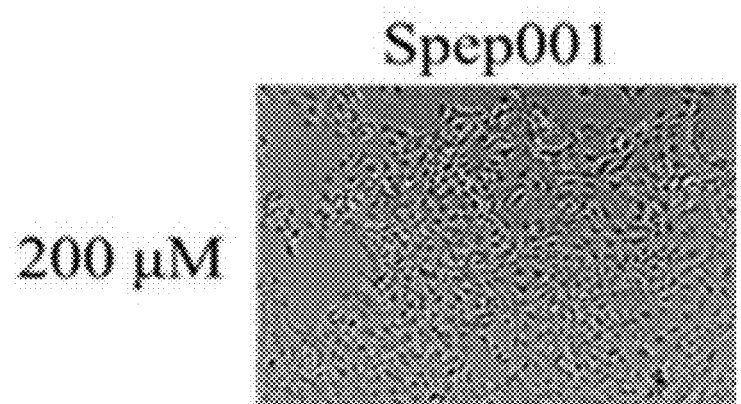

*FIG. 2A(xi)*
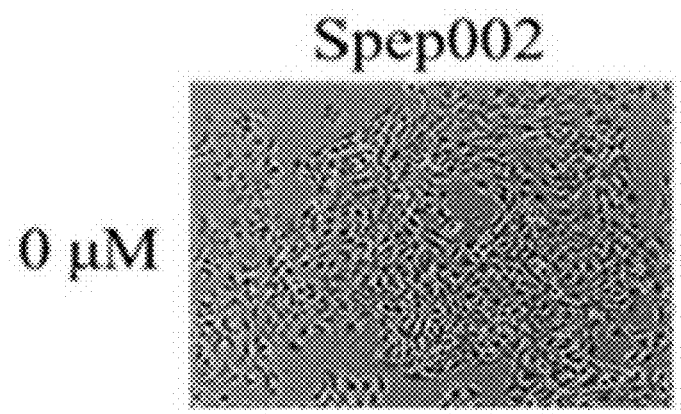
*FIG. 2A(xii)*
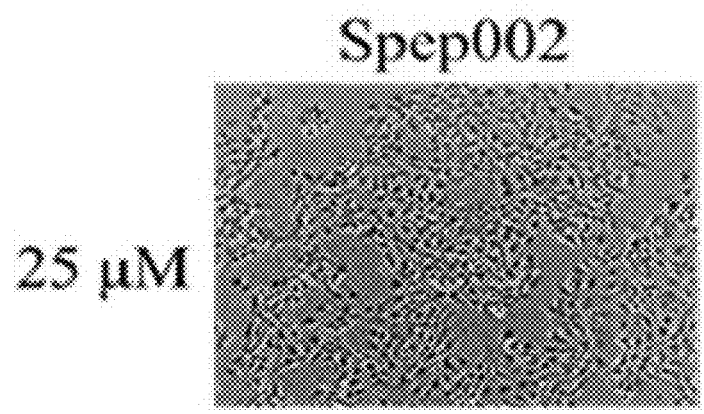
*FIG. 2A(xiii)*
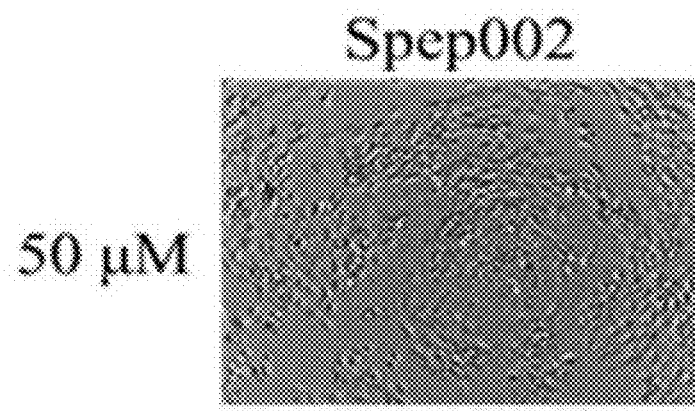

FIG. 2A(xiv)
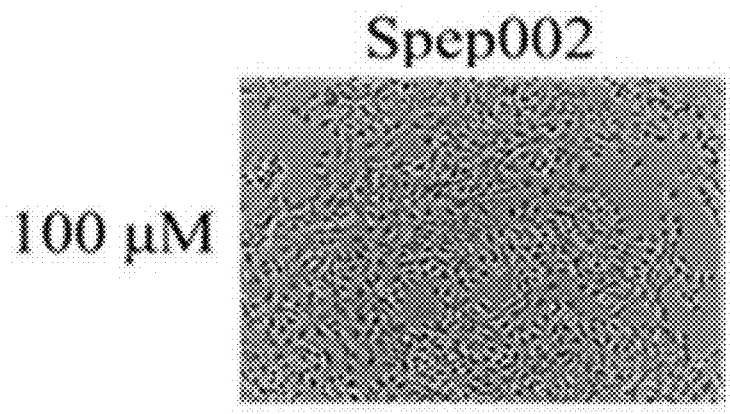
FIG. 2A(xv)
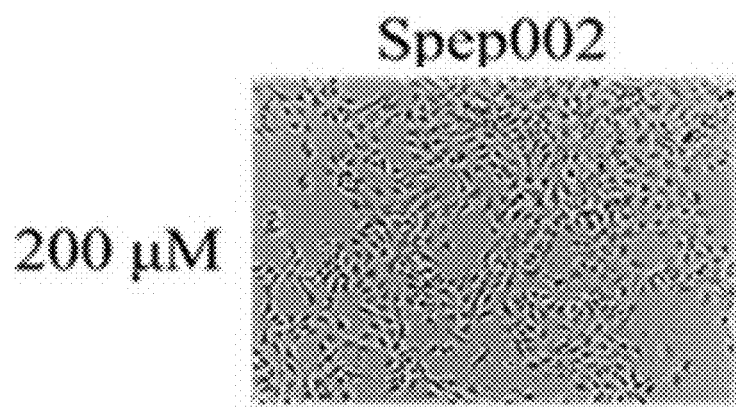
FIG. 2A(xvi)
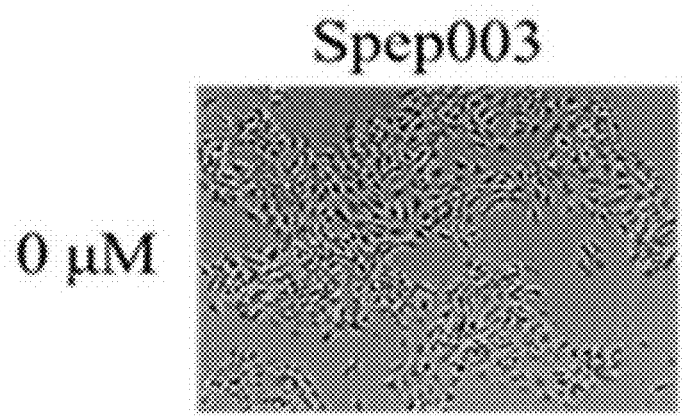

FIG. 2A(xvii)
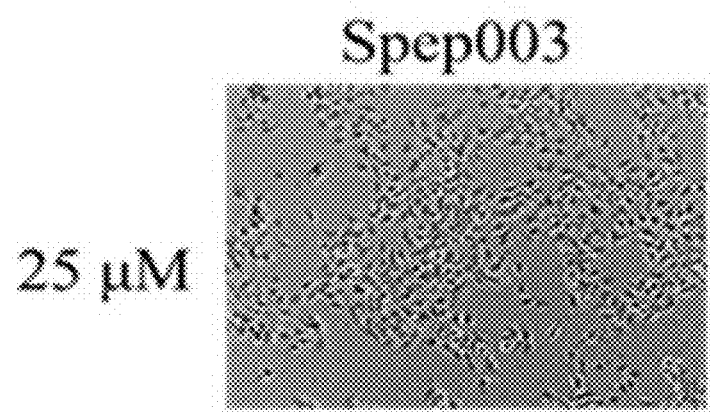
FIG. 2A(xviii)
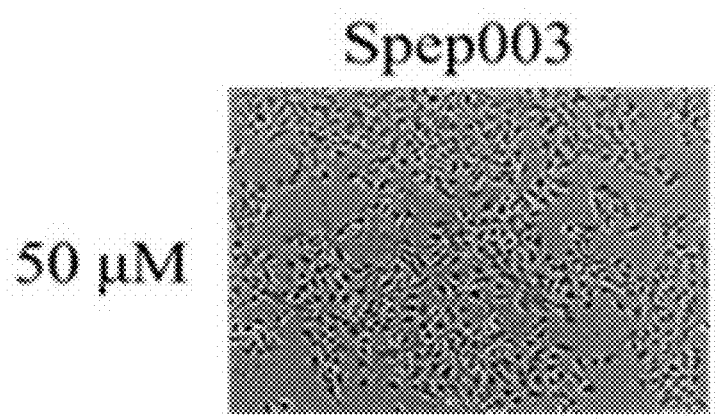

FIG. 2A(xix)
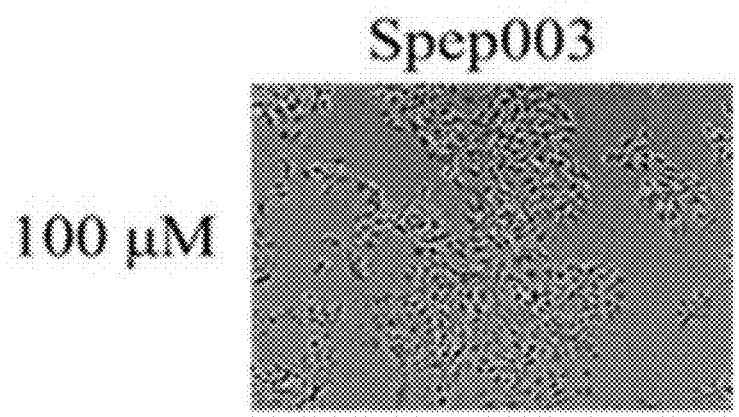
Spep003
100 µM
FIG. 2A(xx)
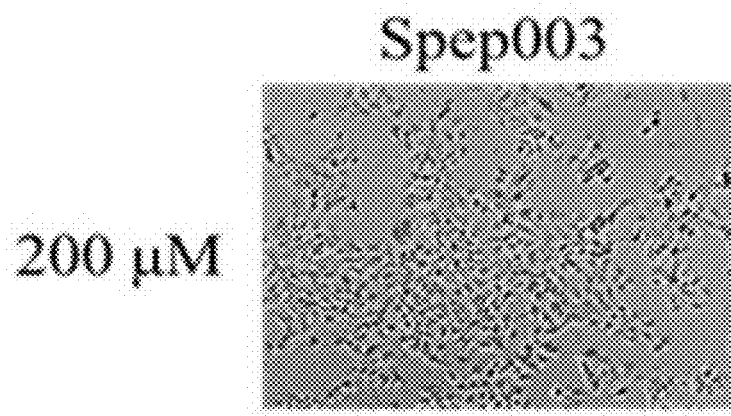
Spep003
200 µM FIG. 3A(ii)
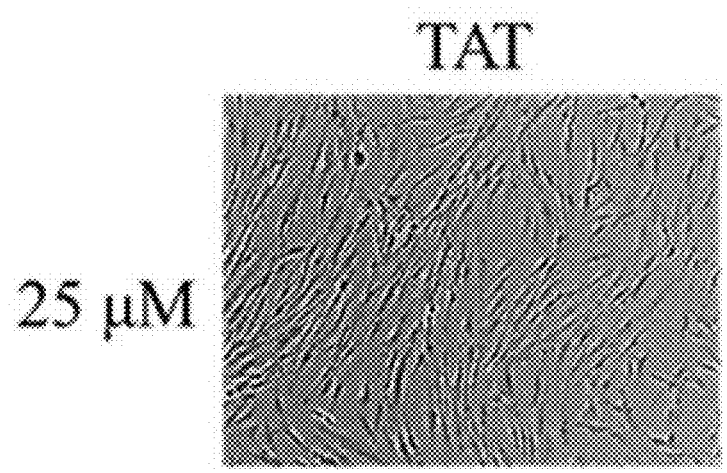
FIG. 3A(iii)
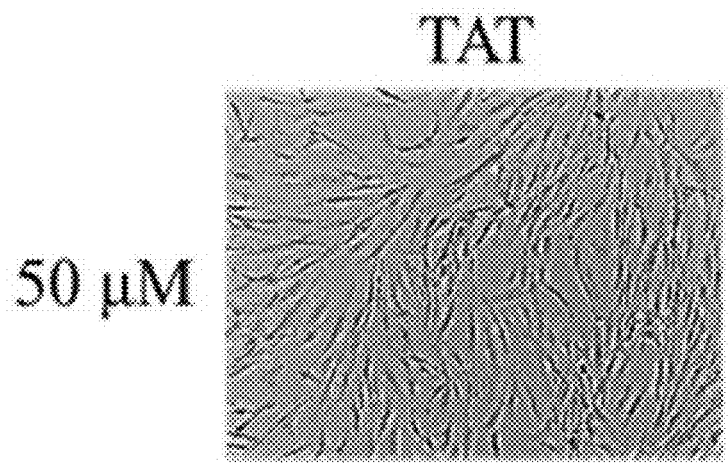

FIG. 3A(iv)
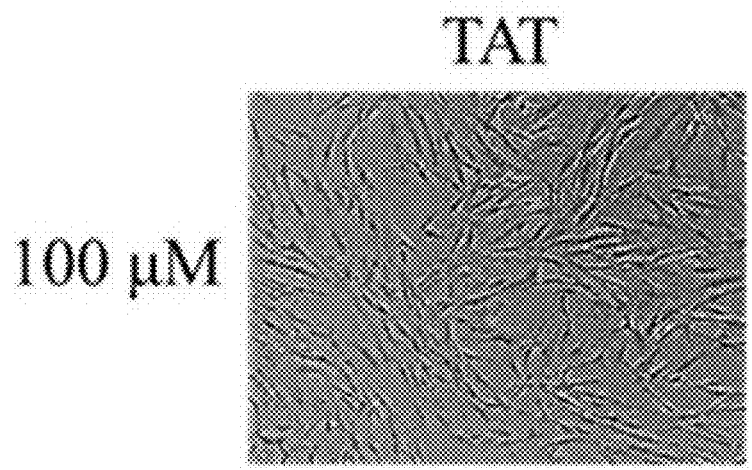
FIG. 3A(v)
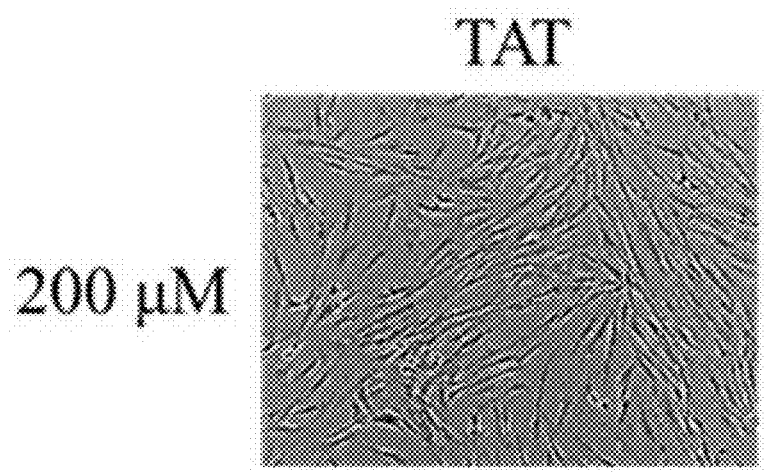

FIG. 3A(vi)
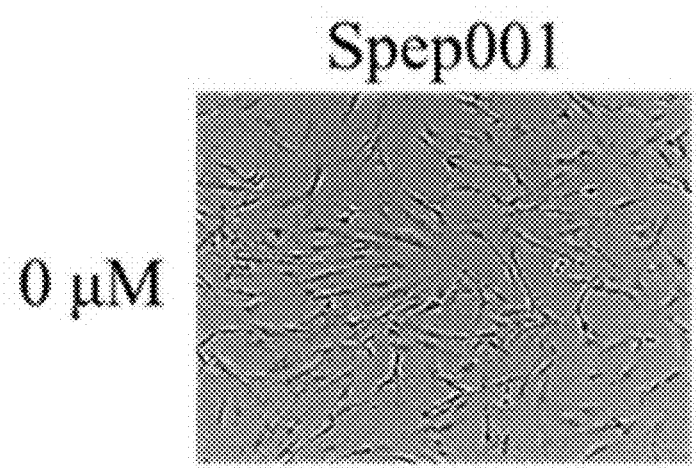
Spep001 0 μM
FIG. 3A(vii)
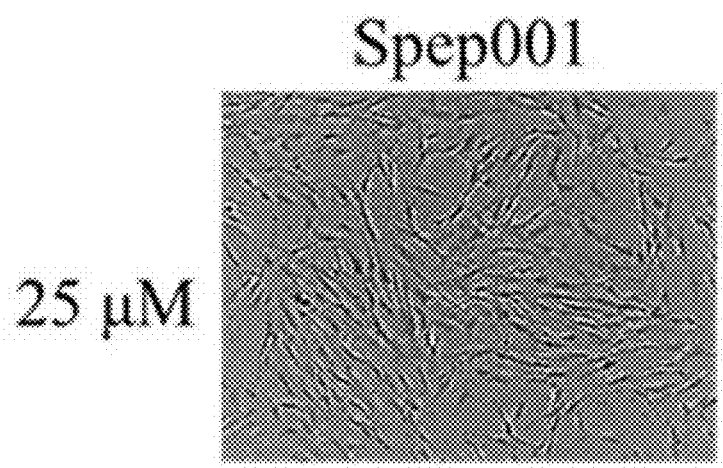
Spep001 25 μM

*FIG. 3A(viii)*
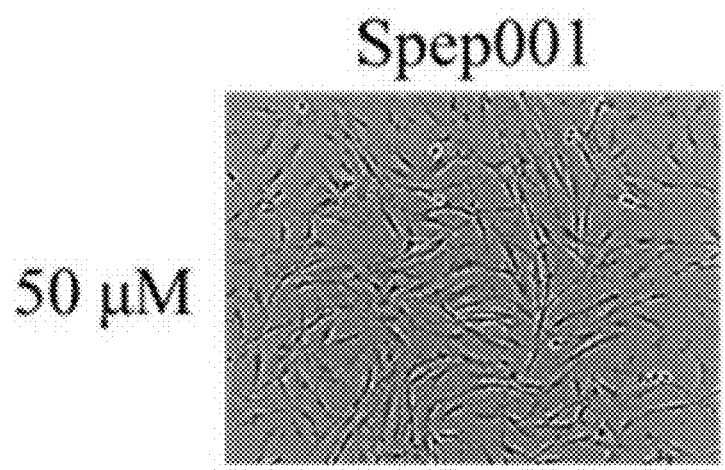
*FIG. 3A(ix)*
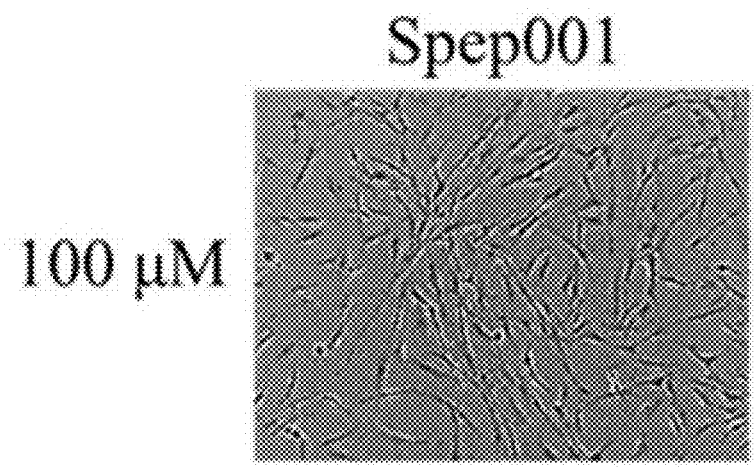

Spep001

Spep002

0 μM

FIG. 3A(xii)
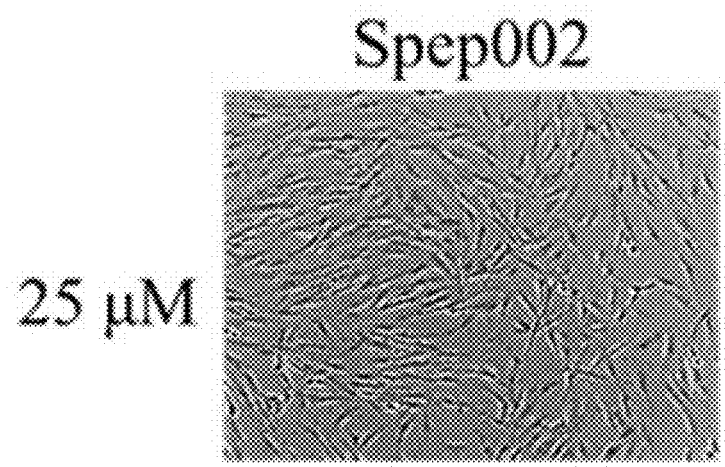
FIG. 3A(xiii)
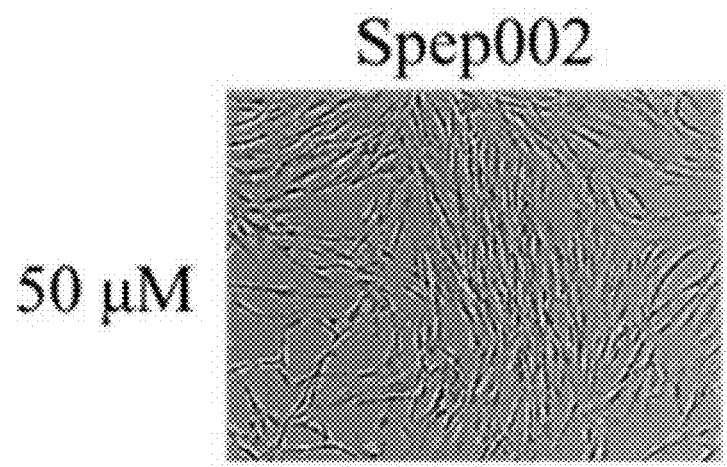

FIG. 3A(xiv)
Spep002
100 μM
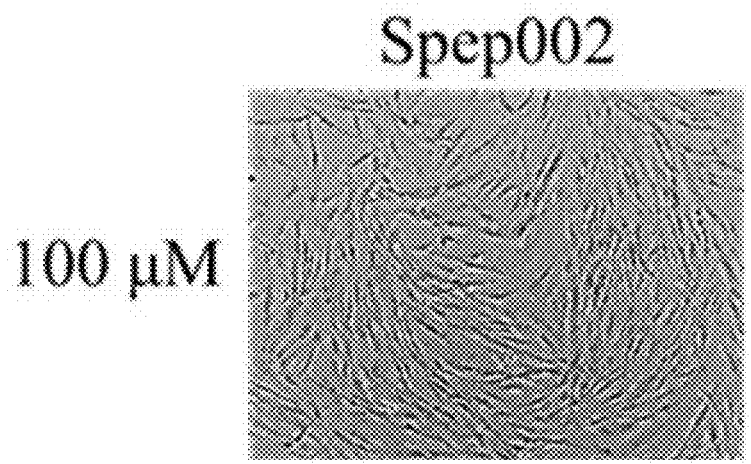
FIG. 3A(xv)
Spep002
200 μM
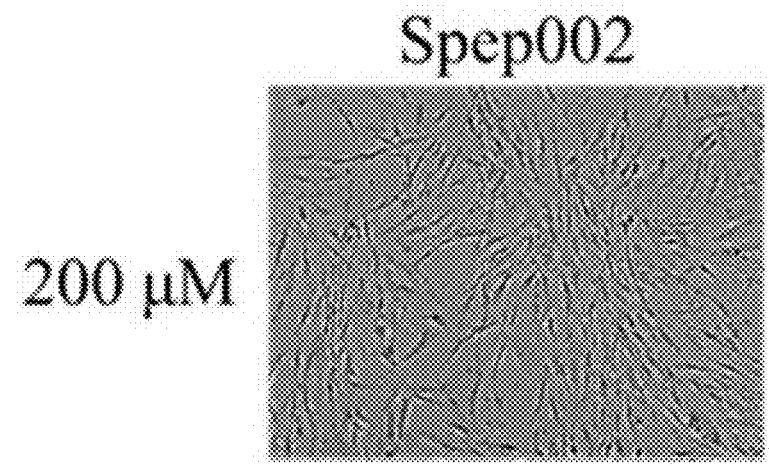

*FIG. 3A(xvi)*
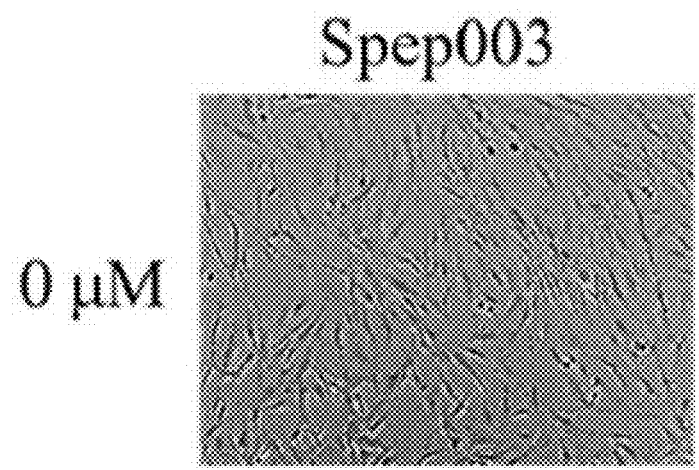
*FIG. 3A(xvii)*
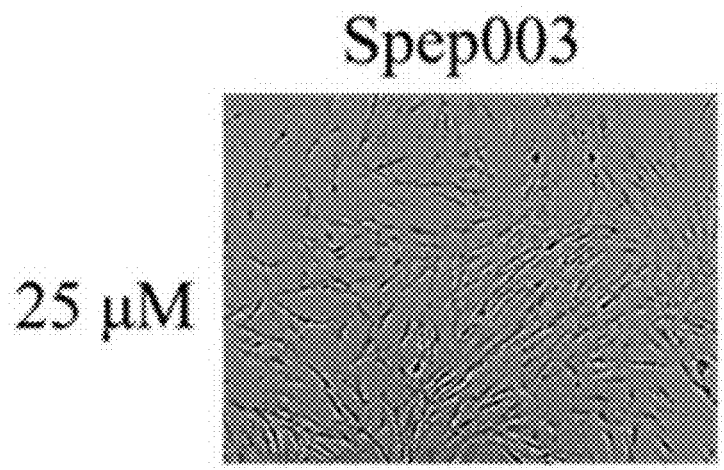

FIG. 3A(xviii)
Spep003
50 μM
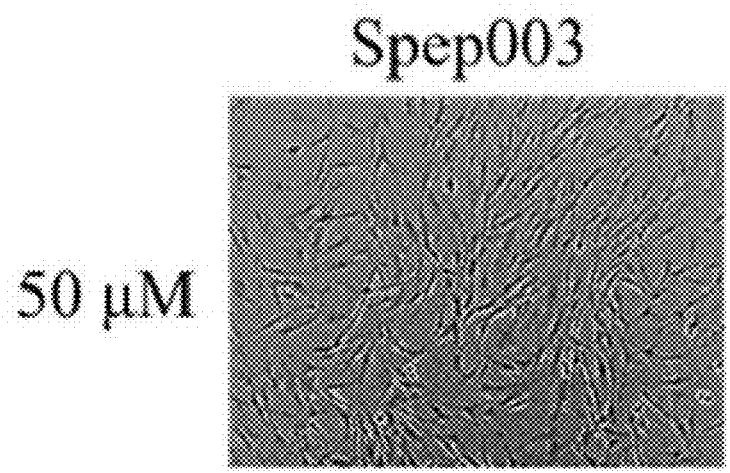
FIG. 3A(xix)
Spep003
100 μM
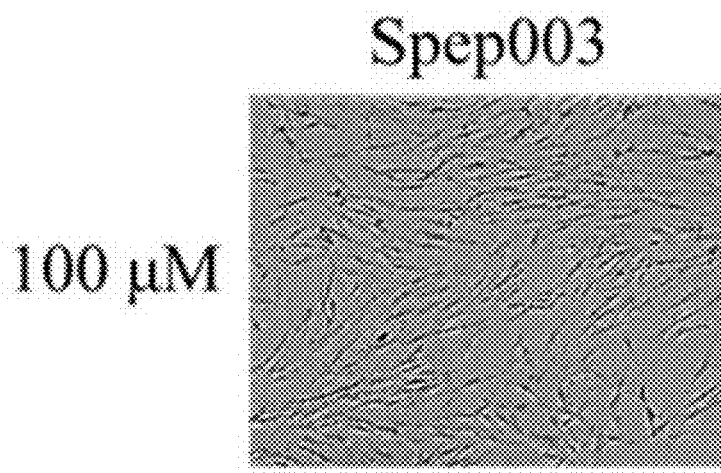

FIG. 3A(xx)
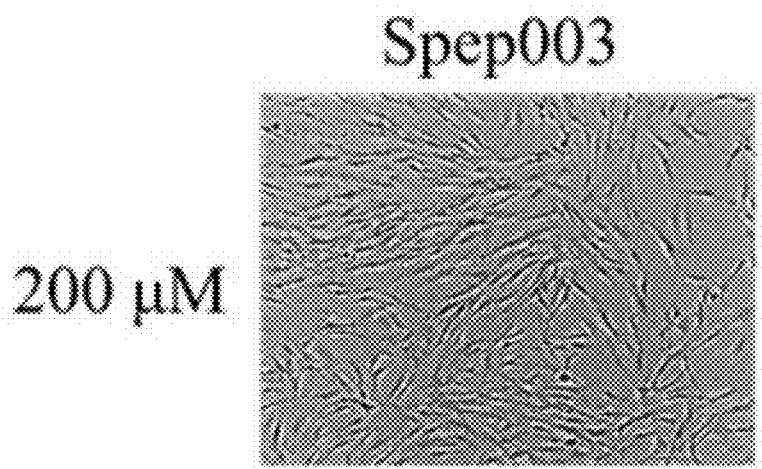
FIG. 3B
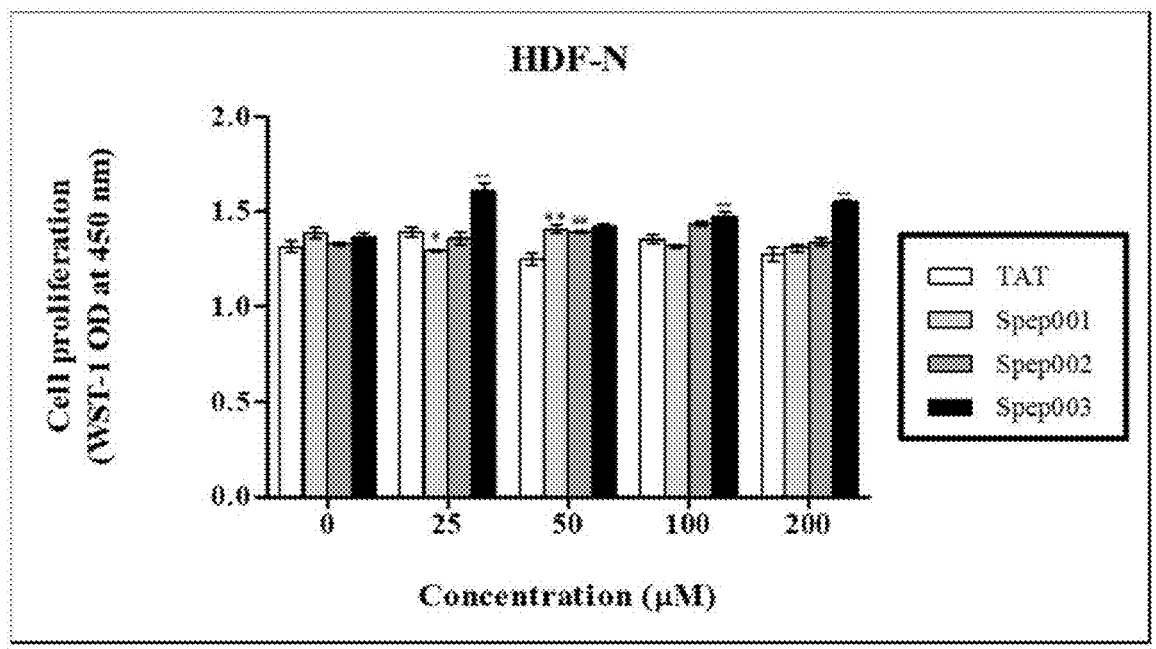

*FIG. 4A(ii)*

FIG. 4A(iii)
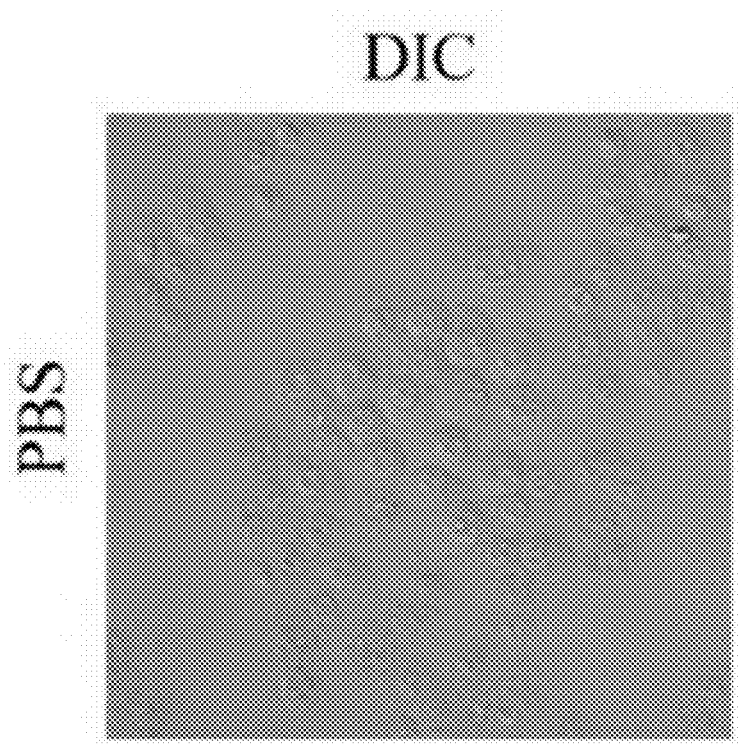
FIG. 4A(iv)
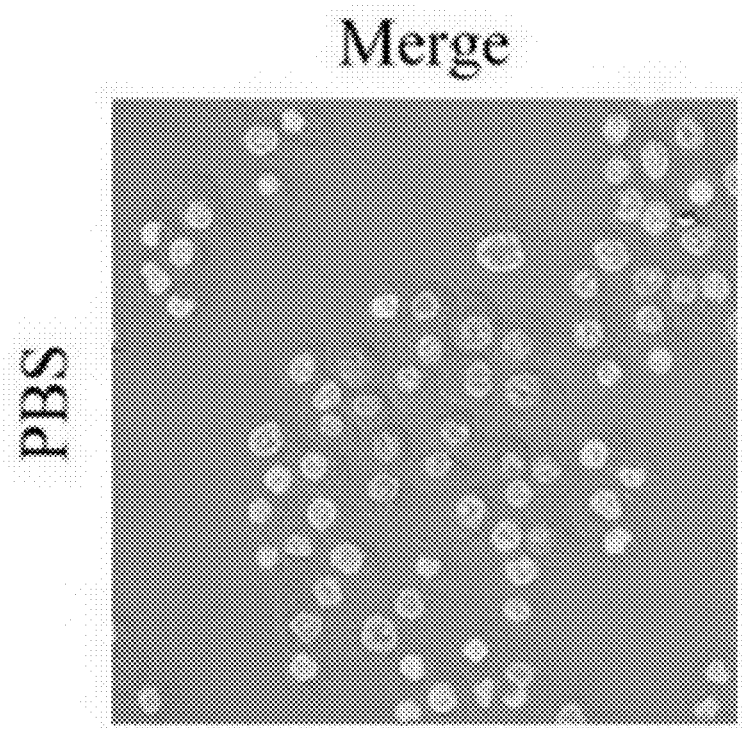

FIG. 4B(ii)
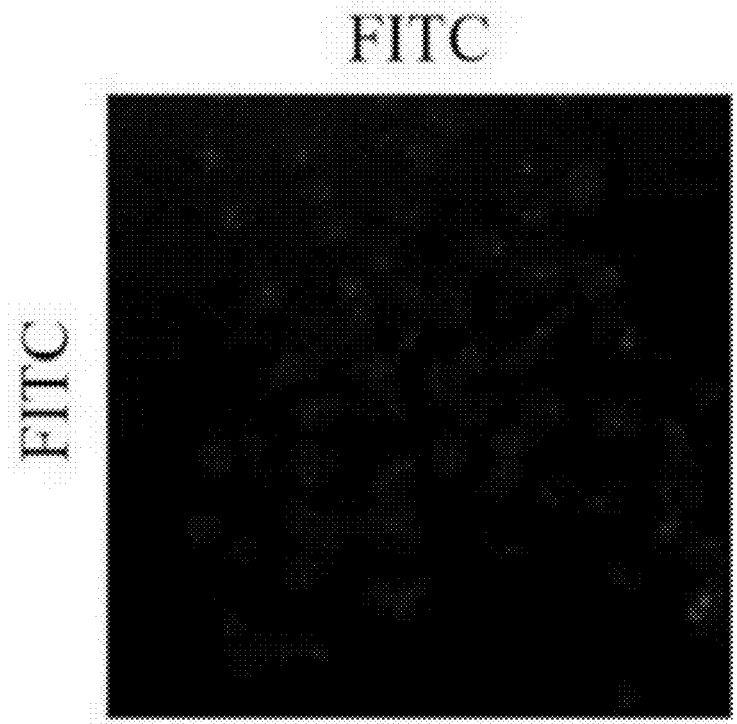
FIG. 4B(iii)
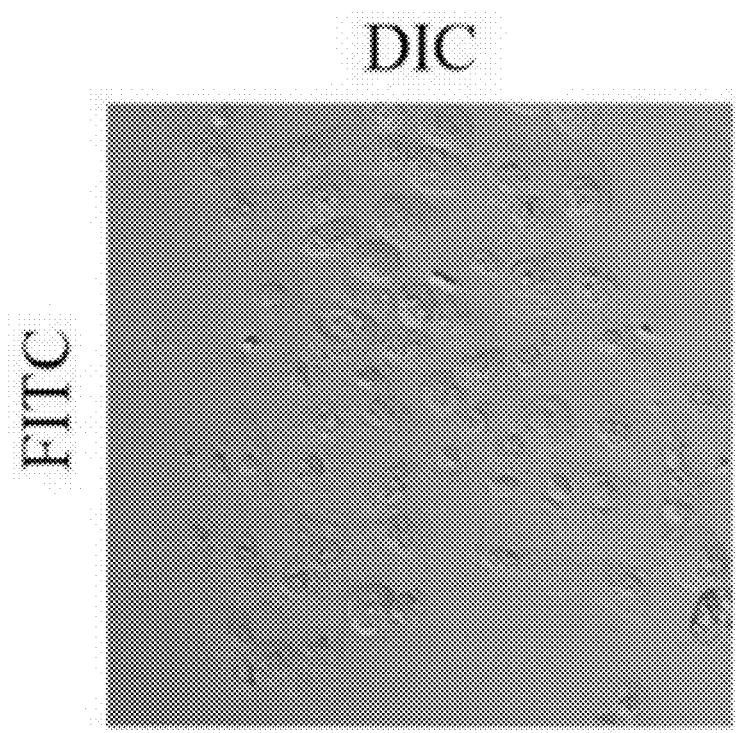

FIG. 4B(iv)
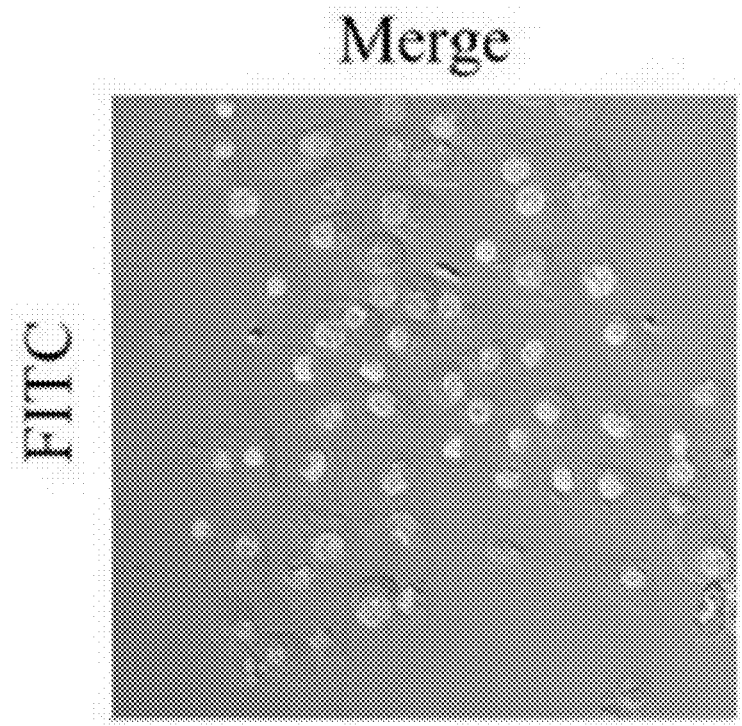

*FIG. 4C(ii)*
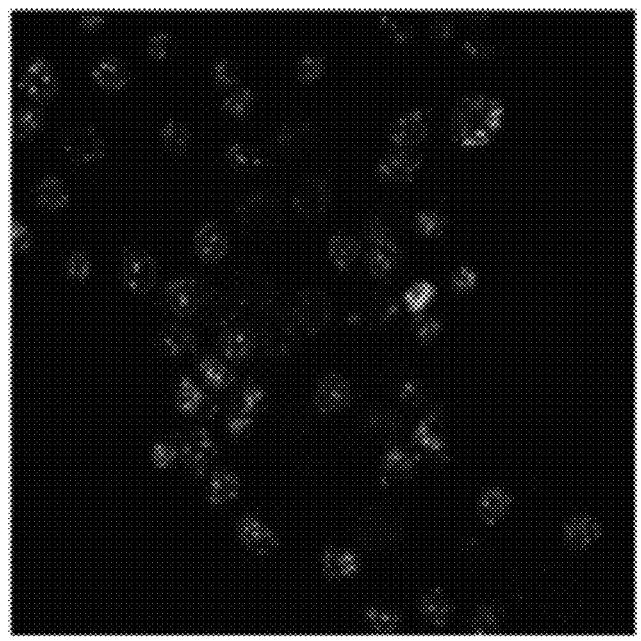

FIG. 4C(iii)
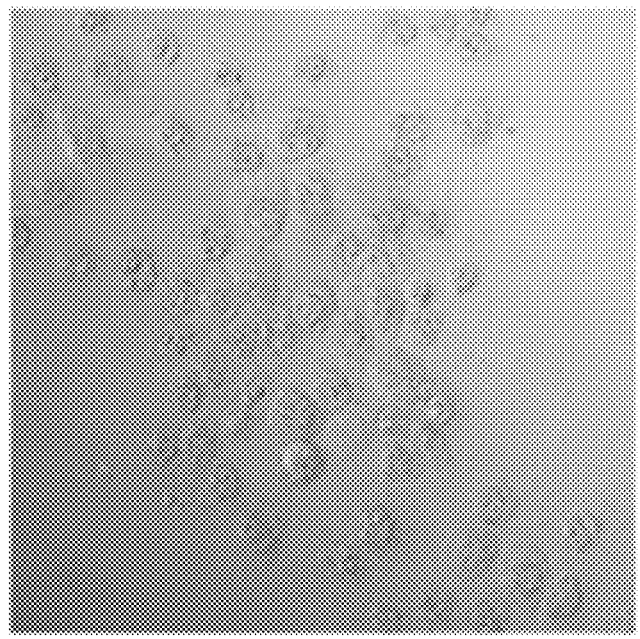

FIG. 4C(iv)
FIG. 4D(i)
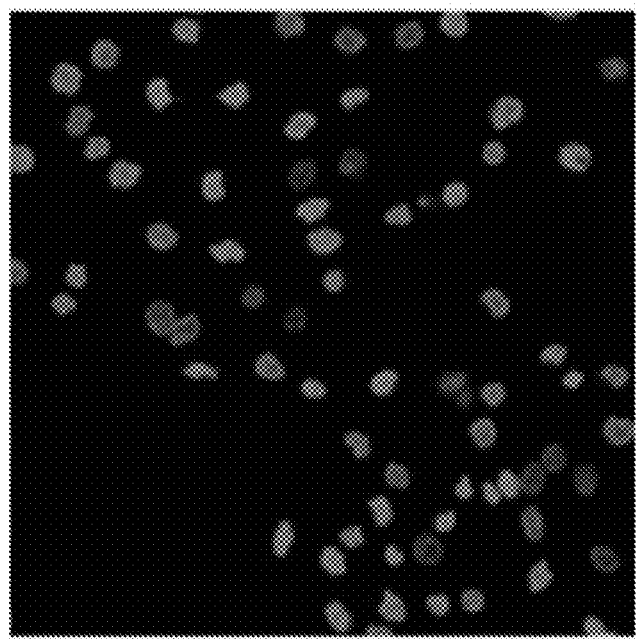

FIG. 4D(ii)
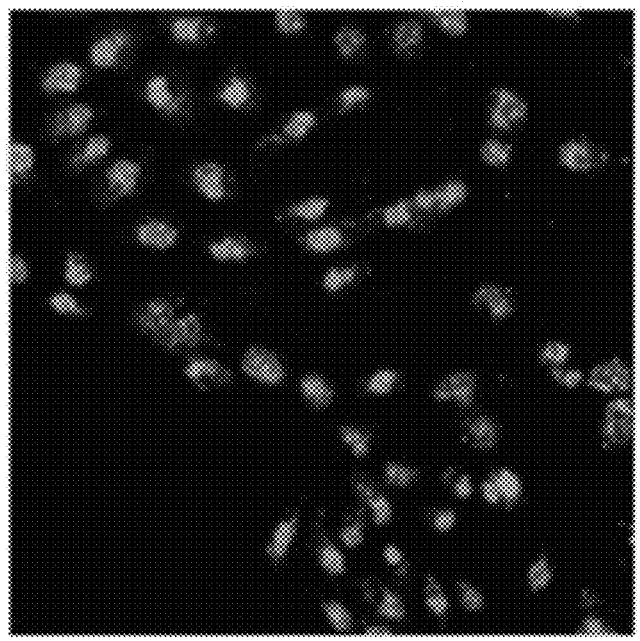

FIG. 4D(iii)
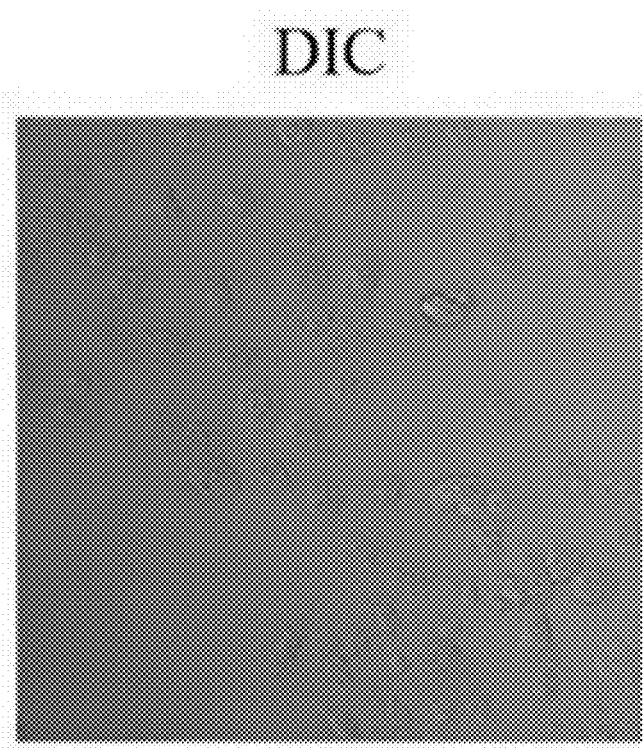
FIG. 4D(iv)
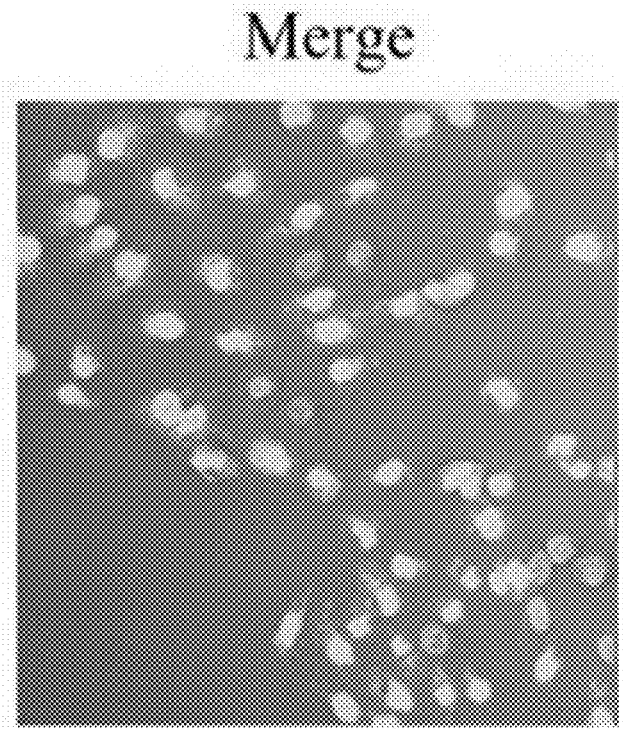

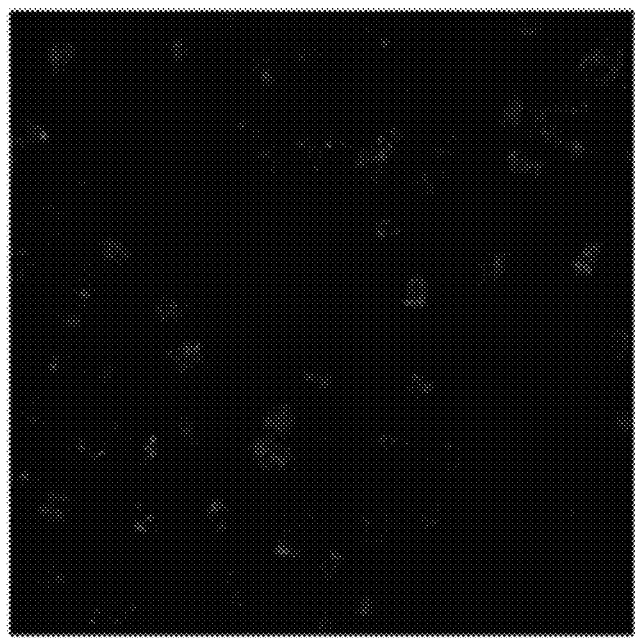
FIG. 4E(ii)

*FIG. 4E(iii)*
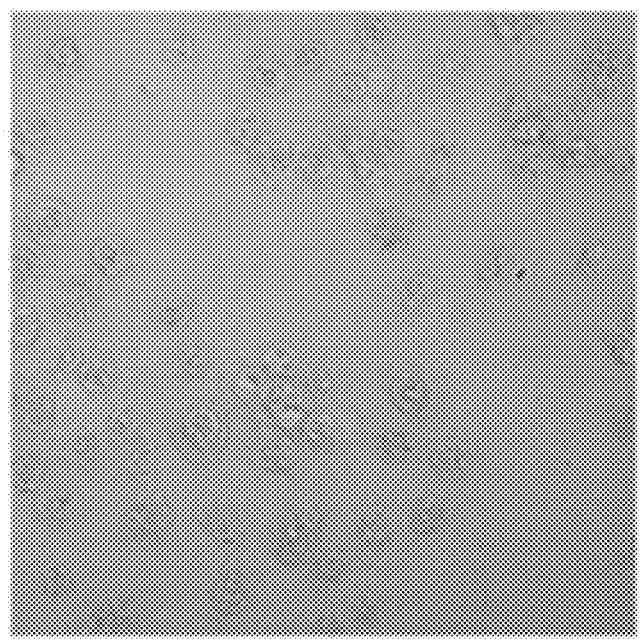

FIG. 4E(iv)
Merge
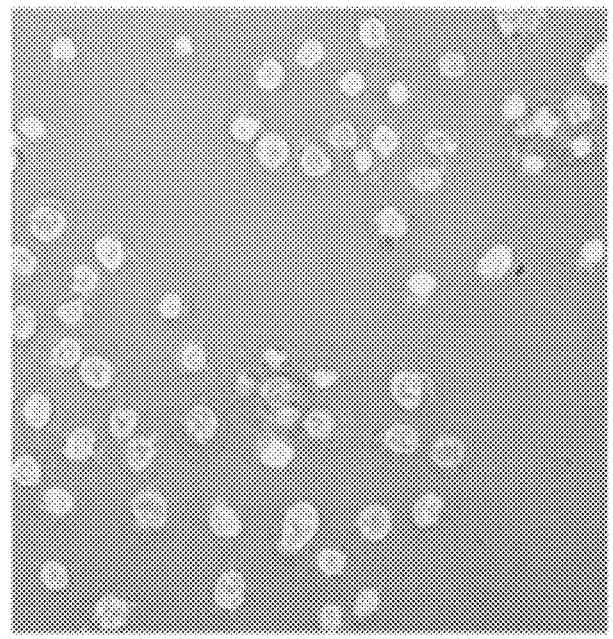
FITC - SPEP002
FIG. 4F(i)
H33342
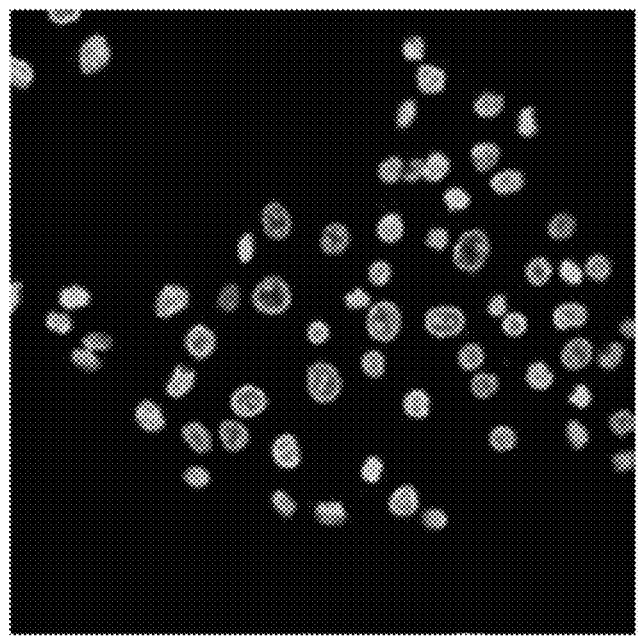
FITC - SPEP003

FIG. 4F(ii)
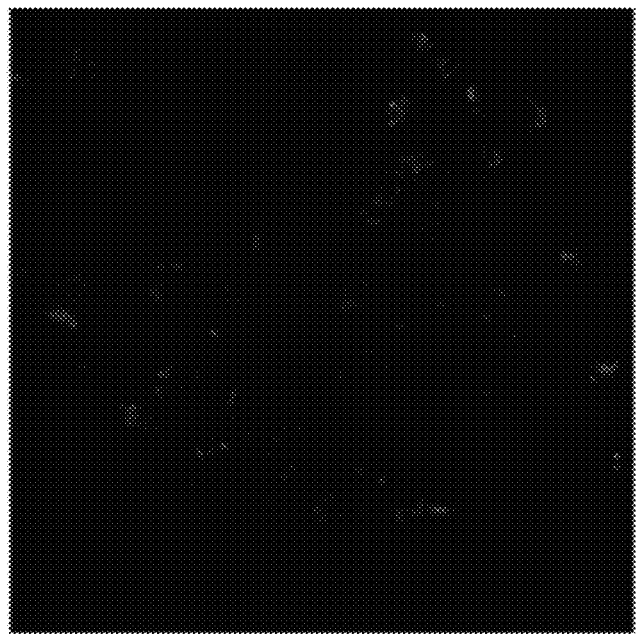

FIG. 4F(iii)
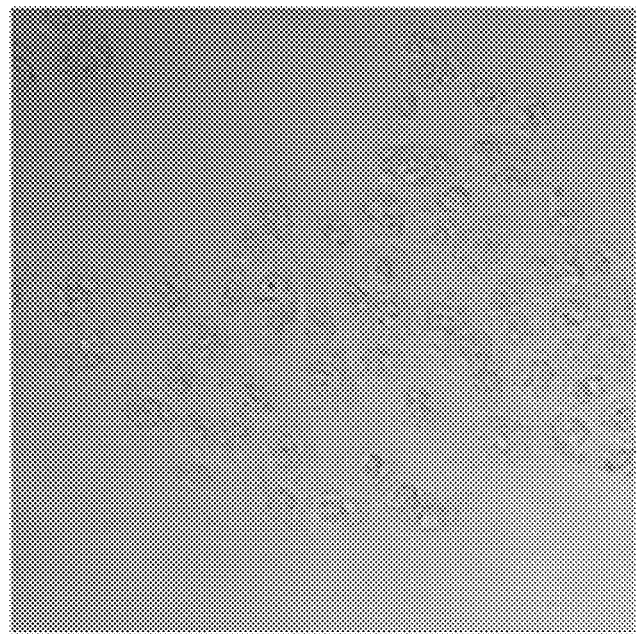

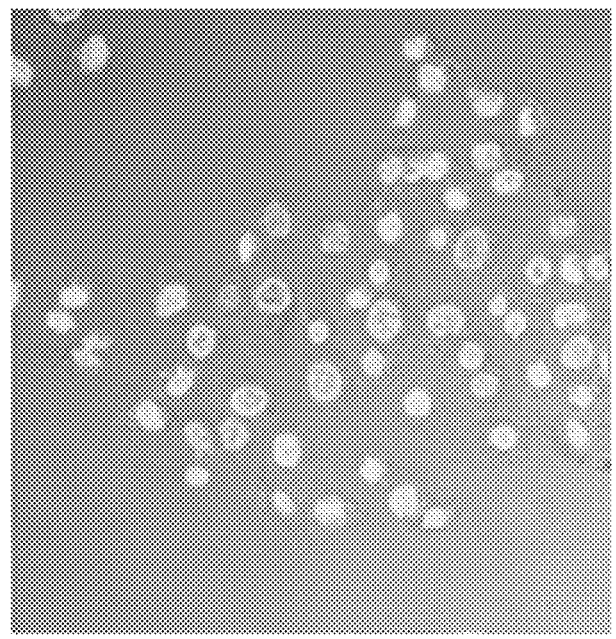
FIG. 4F(iv)

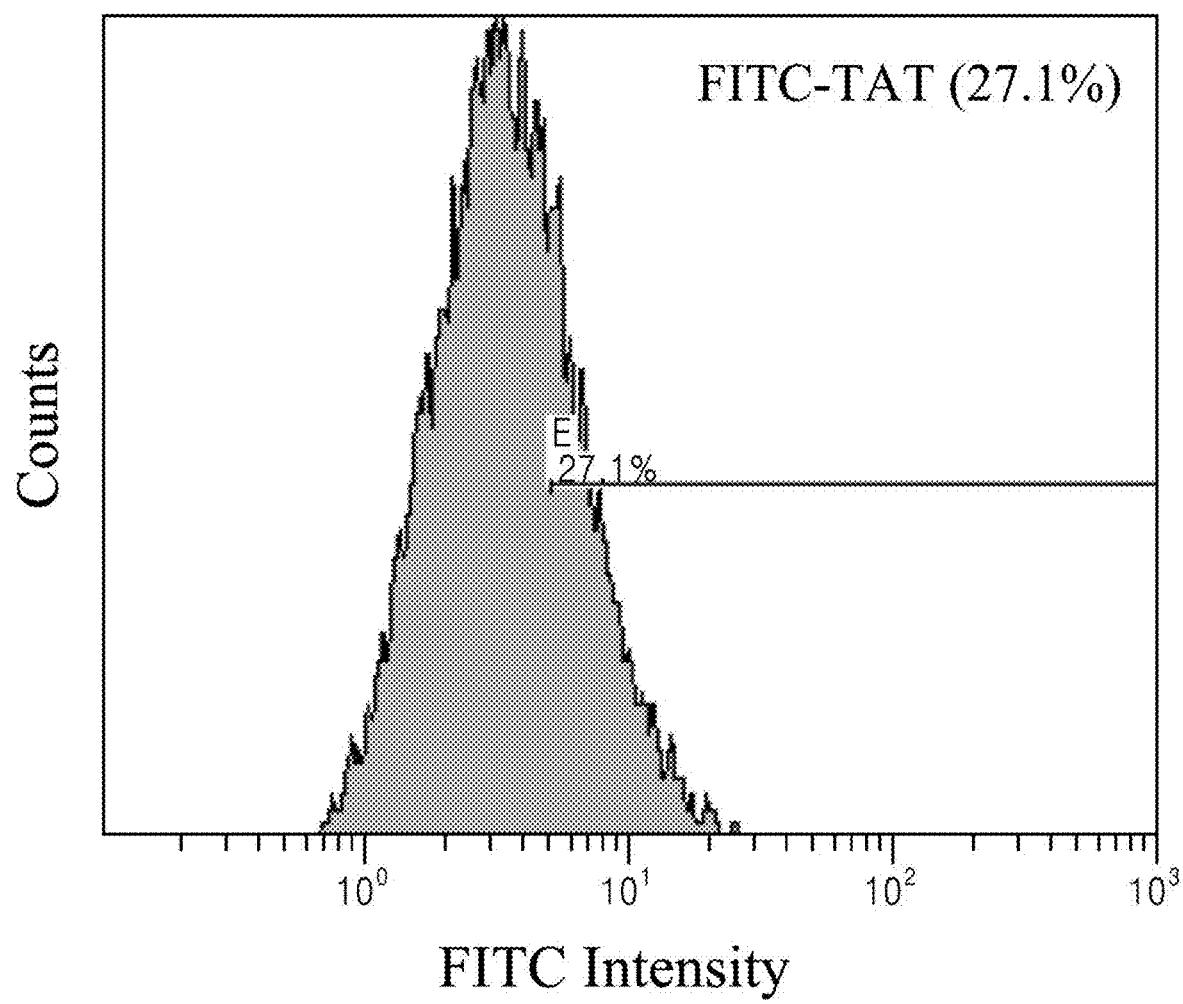
FIG. 5A(ii)

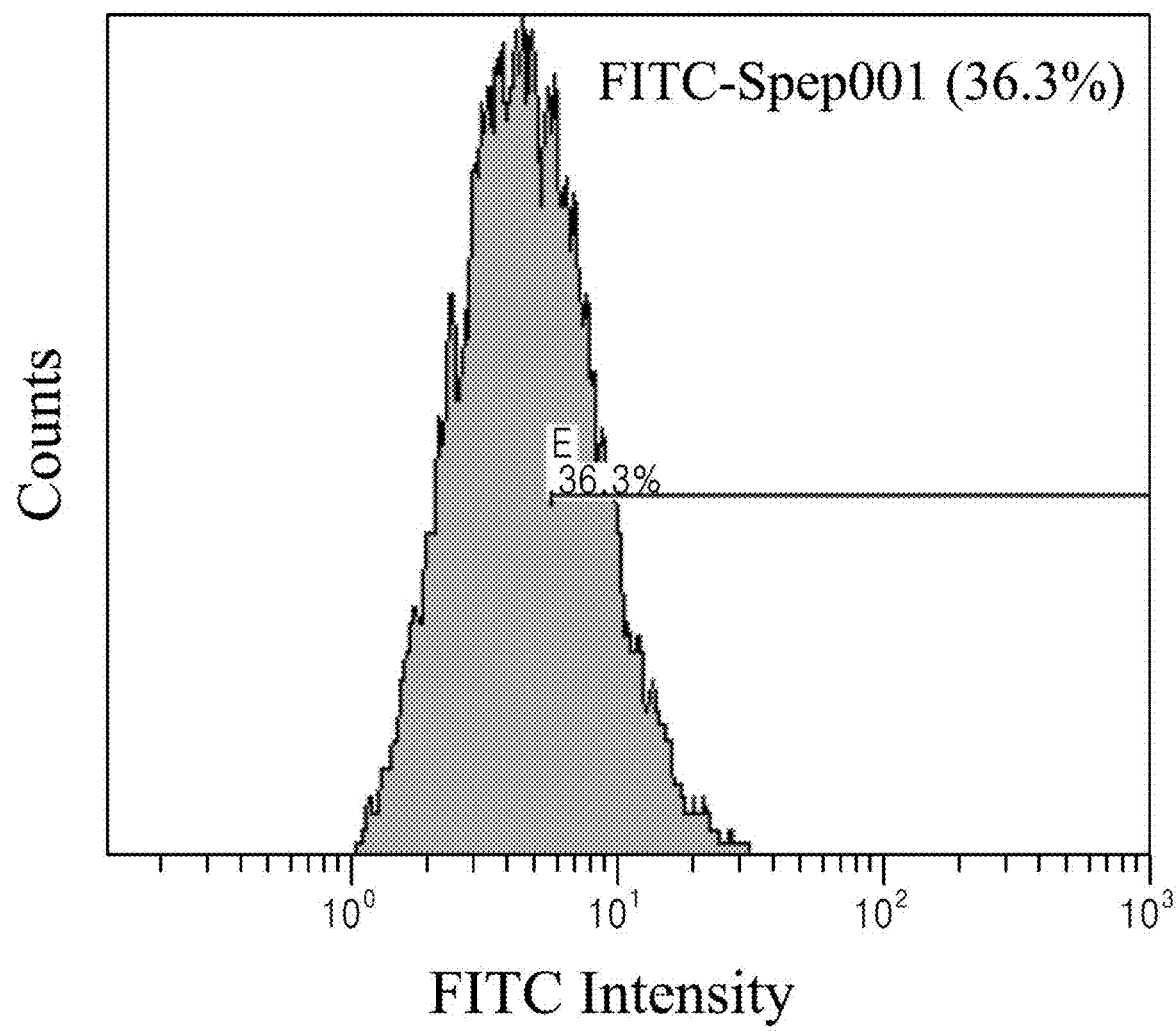
FIG. 5A(iii)

FIG. 5A(iv)
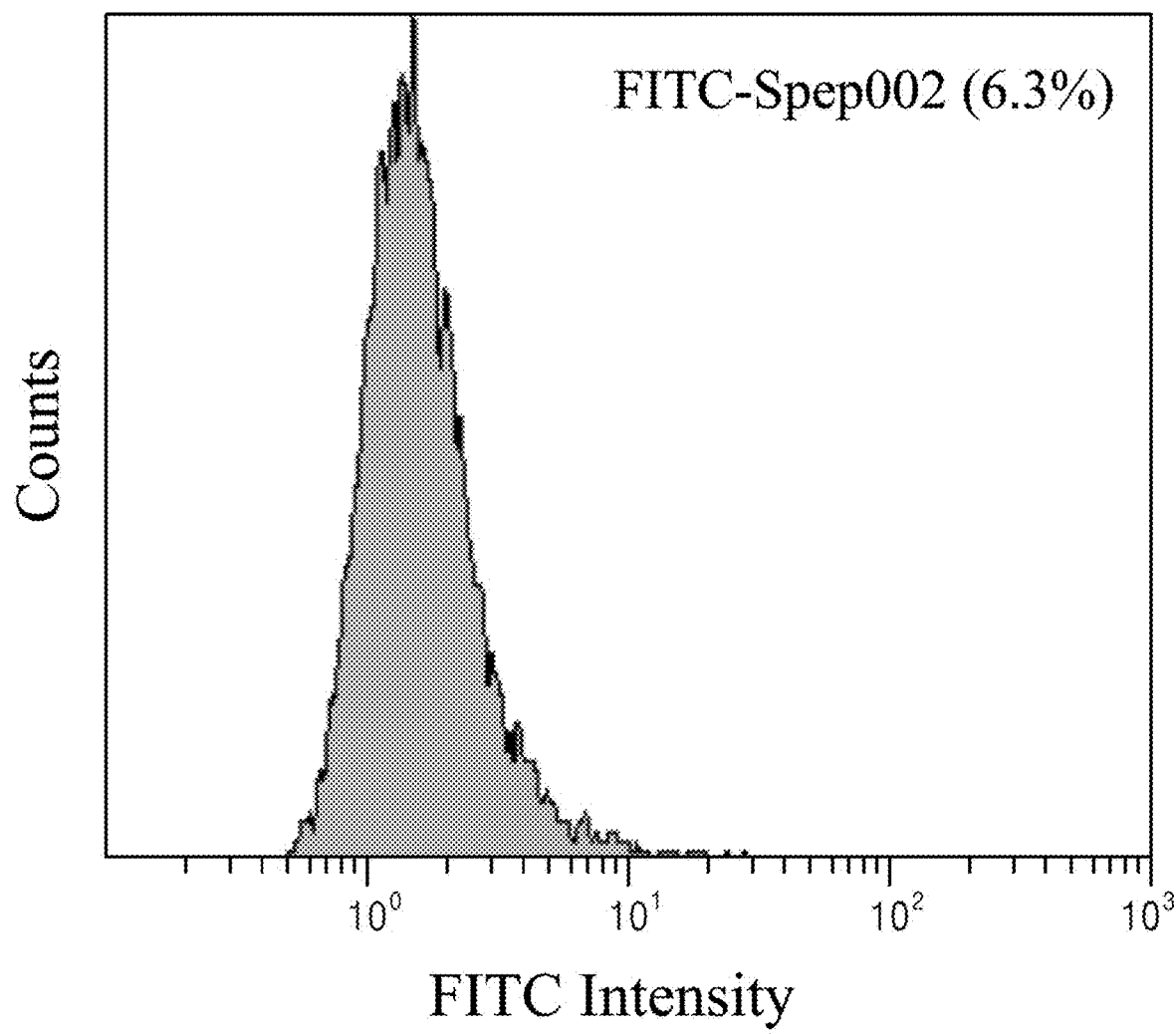

FIG. 8A(ii)
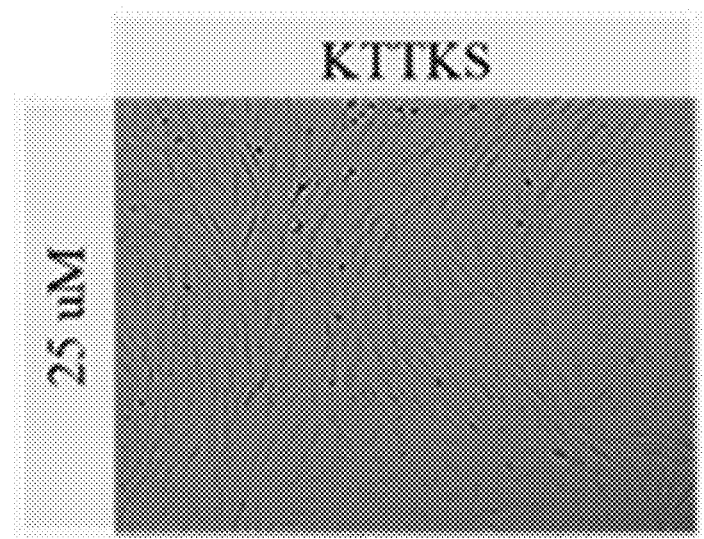
FIG. 8A(iii)
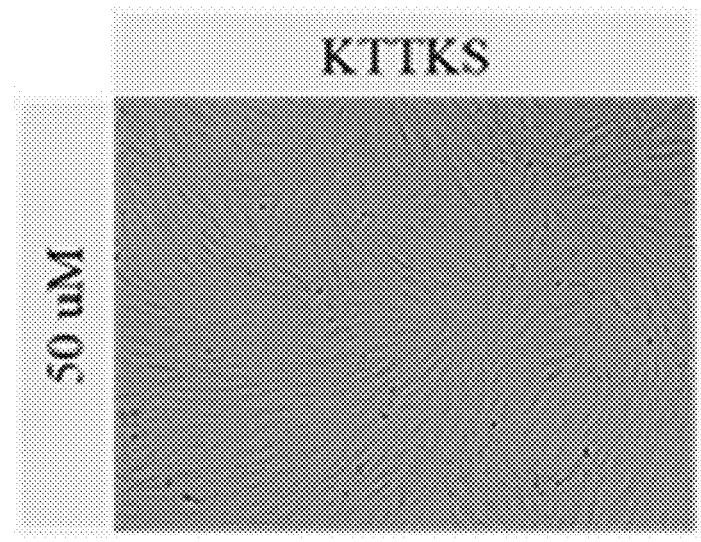

*FIG. 8A(iv)*
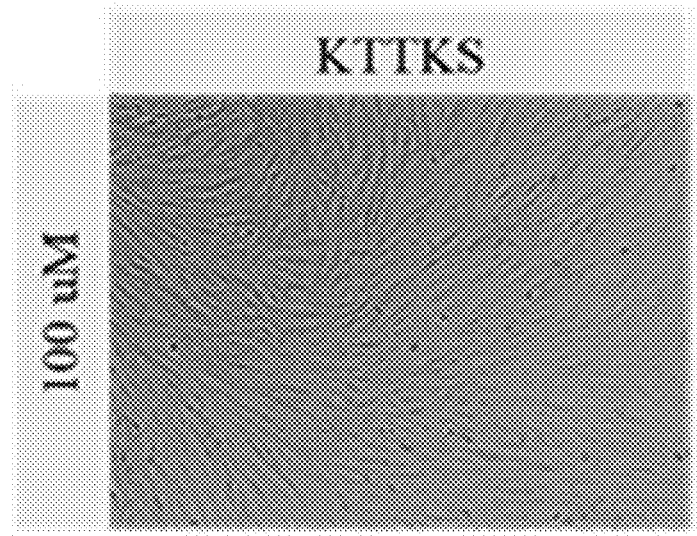
*FIG. 8A(v)*
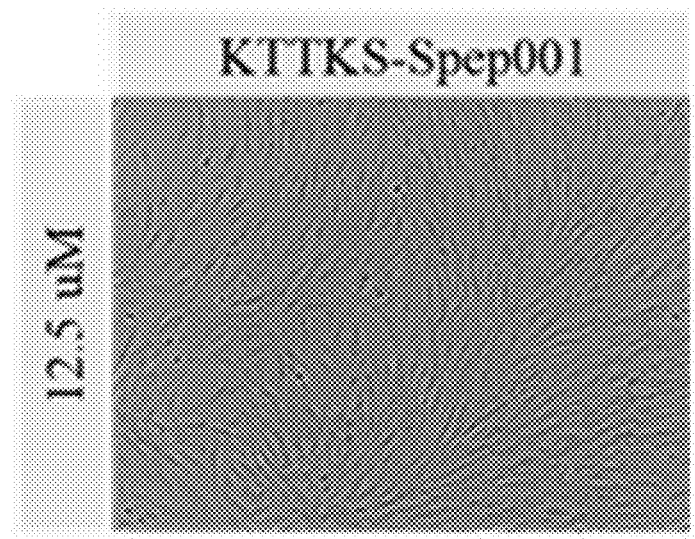

FIG. 8A(vi)
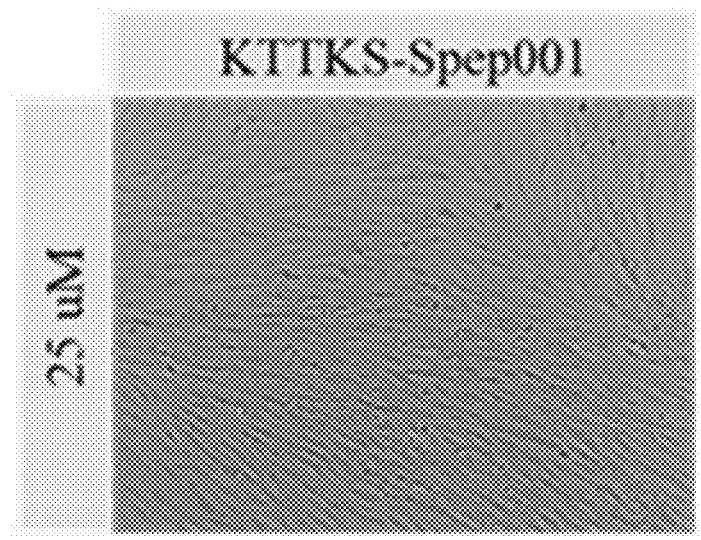
FIG. 8A(vii)
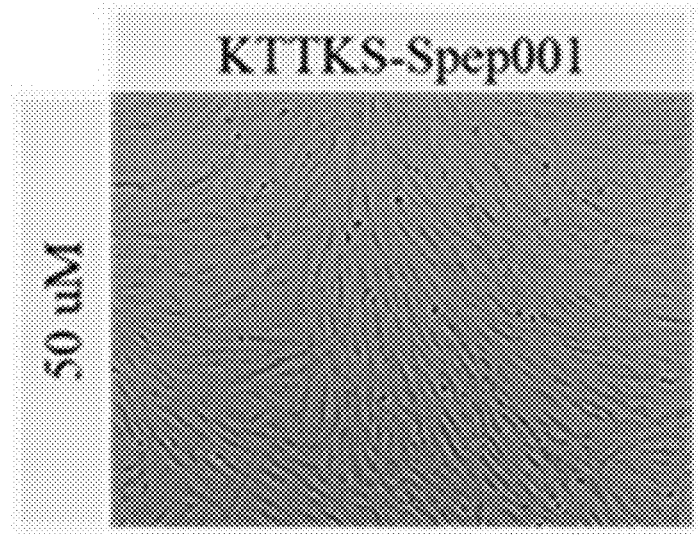

*FIG. 8A(viii)*
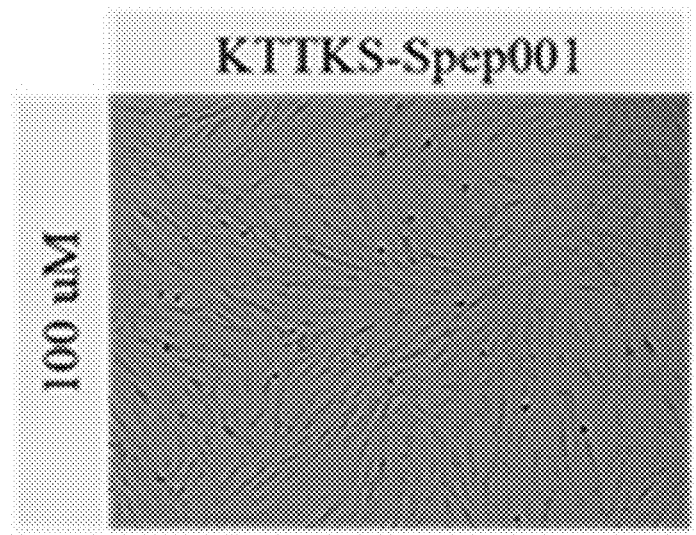
*FIG. 8A(ix)*
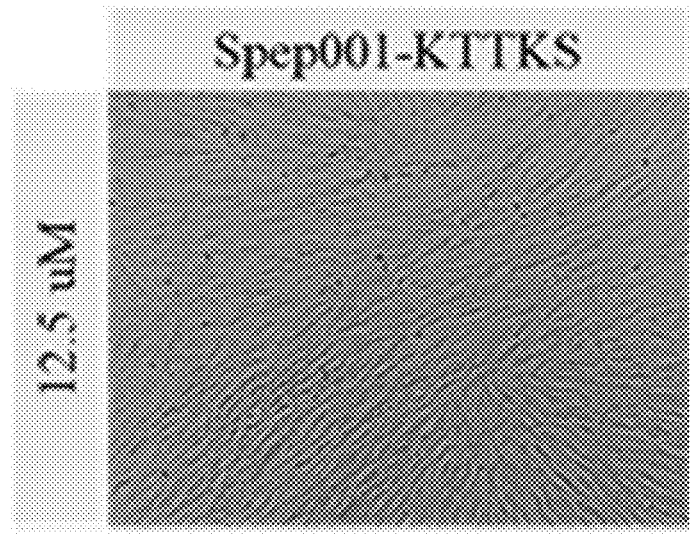

FIG. 8A(xi)

FIG. 8A(xii)
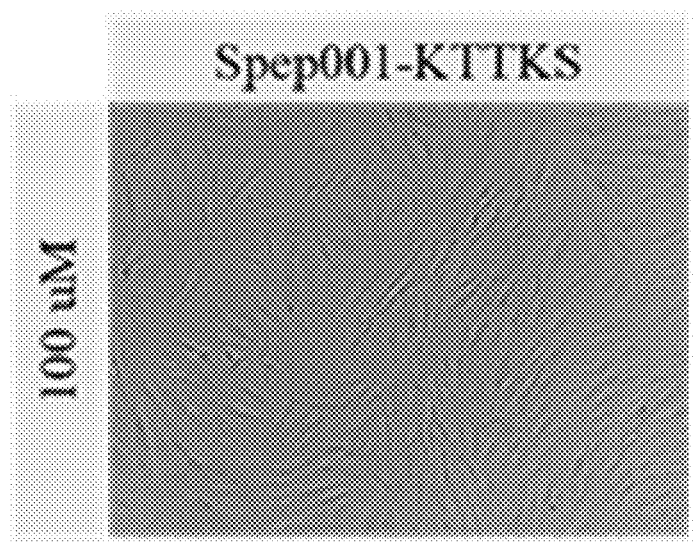
FIG. 8B
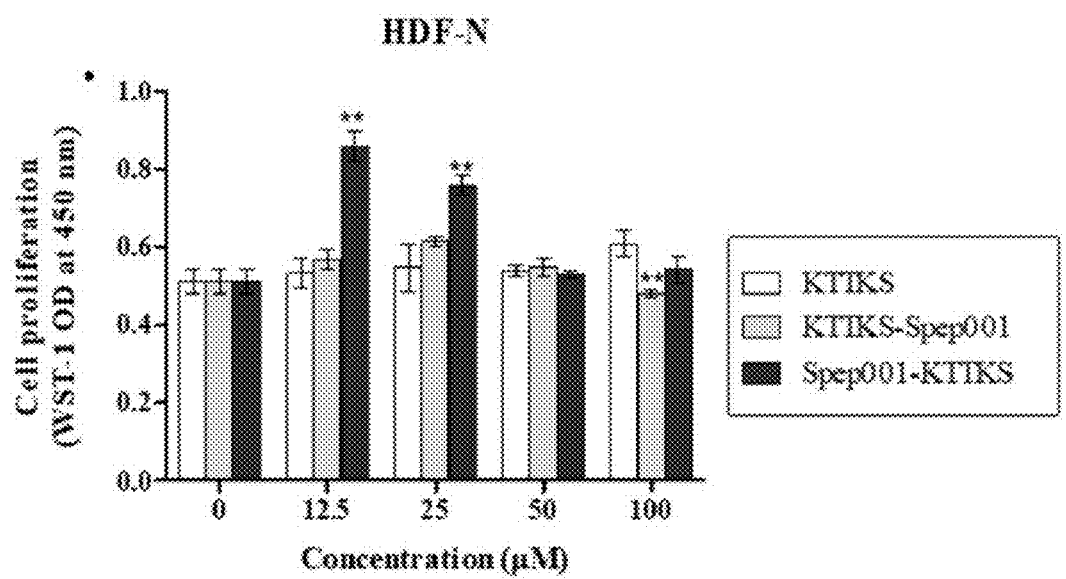

FIG. 9A(ii)

FIG. 9A(iii)
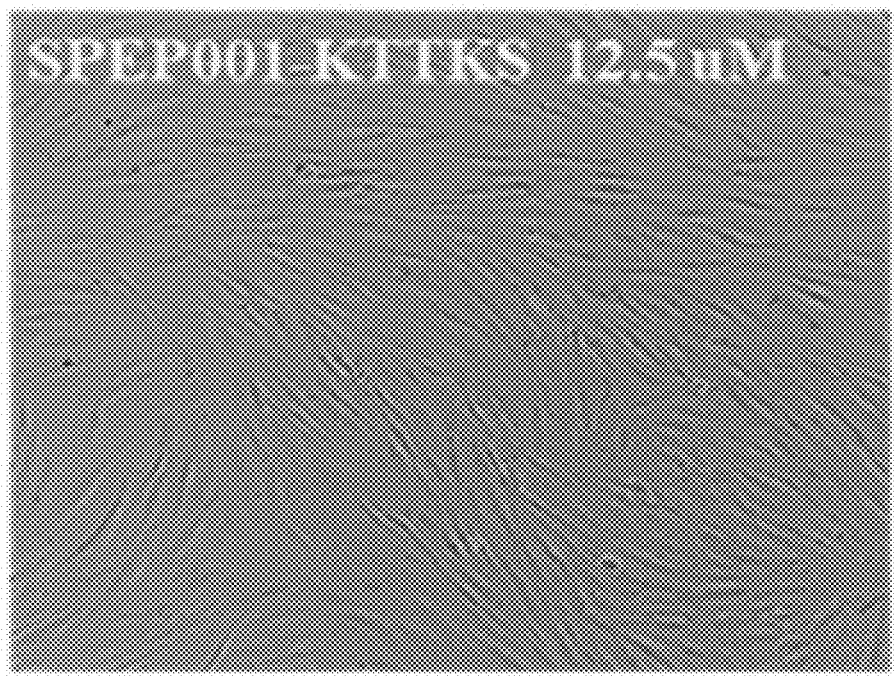
FIG. 9A(iv)
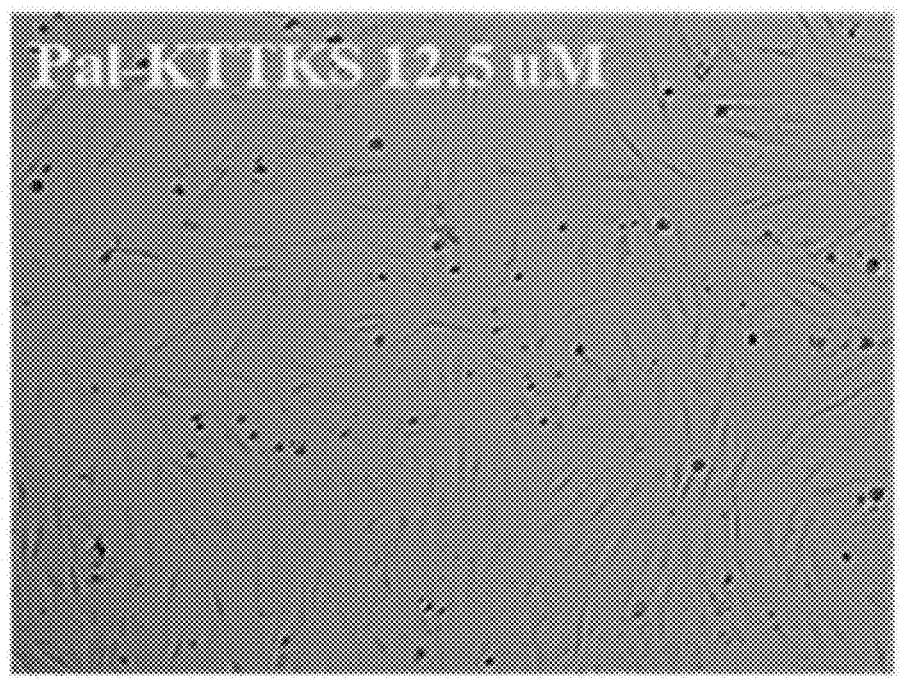

SEQUENCE LISTING

```
Sequence total quantity: 10
SEQ ID NO: 1            moltype = AA  length = 10
FEATURE                 Location/Qualifiers
source                  1..10
                        mol_type = protein
                        organism = synthetic construct
SEQUENCE: 1
RLRLRQRRRR                                                                      10

SEQ ID NO: 2            moltype = RNA  length = 30
FEATURE                 Location/Qualifiers
source                  1..30
                        mol_type = other RNA
                        organism = synthetic construct
SEQUENCE: 2
cgcctgcgcc tgcgccagcg ccgccgccgc                                                30

SEQ ID NO: 3            moltype = RNA  length = 30
FEATURE                 Location/Qualifiers
source                  1..30
                        mol_type = other RNA
                        organism = synthetic construct
SEQUENCE: 3
cggctgcggc tgcggcagcg gcggcggcgg                                                30

SEQ ID NO: 4            moltype = RNA  length = 30
FEATURE                 Location/Qualifiers
source                  1..30
                        mol_type = other RNA
                        organism = synthetic construct
SEQUENCE: 4
aggctgaggc tgaggcagag gaggaggagg                                                30

SEQ ID NO: 5            moltype = AA  length = 5
FEATURE                 Location/Qualifiers
source                  1..5
                        mol_type = protein
                        organism = synthetic construct
SEQUENCE: 5
KTTKS                                                                           5

SEQ ID NO: 6            moltype = AA  length = 15
FEATURE                 Location/Qualifiers
source                  1..15
                        mol_type = protein
                        organism = synthetic construct
SEQUENCE: 6
RLRLRQRRRR KTTKS                                                                15

SEQ ID NO: 7            moltype = AA  length = 15
FEATURE                 Location/Qualifiers
source                  1..15
                        mol_type = protein
                        organism = synthetic construct
SEQUENCE: 7
KTTKSRLRLR QRRRR                                                                15

SEQ ID NO: 8            moltype = AA  length = 10
FEATURE                 Location/Qualifiers
source                  1..10
                        mol_type = protein
                        organism = synthetic construct
SEQUENCE: 8
KRRWRKIPKR                                                                      10

SEQ ID NO: 9            moltype = AA  length = 10
FEATURE                 Location/Qualifiers
source                  1..10
                        mol_type = protein
                        organism = synthetic construct
SEQUENCE: 9
RKRWLRKPRP                                                                      10
```

```
SEQ ID NO: 10          moltype = AA  length = 10
FEATURE                Location/Qualifiers
source                 1..10
                       mol_type = protein
                       organism = synthetic construct
SEQUENCE: 10
YGRKRRQRRR                                                              10
```

CELL-PENETRATING PEPTIDES AND COMPOSITION INCLUDING THE SAME

CROSS-REFERENCE TO RELATED APPLICATION

This application claims the benefit under 35 USC 119(a) of Korean Patent Application No. 10-2022-0016129 filed on Feb. 8, 2022 in the Korean Intellectual Property Office, the entire disclosures of which are incorporated herein by reference for all purposes.

REFERENCE TO AN ELECTRONIC SEQUENCE LISTING

The contents of the electronic sequence listing (OP20220261US.xml; Size: 9,579 bytes; and Date of Creation: Sep. 26, 2022) is herein incorporated by reference in its entirety.

TECHNICAL FIELD

The present disclosure relates to a novel cell-penetrating multifunctional peptide, a composition for drug delivery and a cosmetic composition for skin improvement including the same.

BACKGROUND

Intracellular delivery of therapeutic molecules is very important for drug delivery. In intracellular organelles such as the cytoplasm, nucleus, ribosomes and mitochondria, drugs must pass through cell membranes to exert their therapeutic effect. However, large hydrophilic therapeutic reagents such as proteins or nucleic acids cannot enter cells.

One of the alternatives to solve such a problem is to use a cell-penetrating peptide (CPP). A conjugate in which a targeted drug is conjugated to a CPP, which is a peptide that generally exhibits cell membrane permeability, is used to deliver the targeted drug into cells. Representative examples of CPPB include HIV-1 TAT translocation domain (Green; M. and Loewenstein, P M (1988) Cell 55, 1179-1188) and the homeodomain of the Antennapedia protein (Joliot; A. et al. (1991) Proc. Natl. Acad. Sci. USA 88, 1864-1868), and other various types of CPPs are known and have been developed through continuous research. These CPPs commonly contain a relatively high content of basic amino acids and are amphipathic and generally composed of a sequence of 50 amino acids or less. Also, the CPPs are known to damage or destroy cell membranes by inhibiting the stability of the cell membranes and exhibit cytotoxicity.

Intracellular delivery using a cell-penetrating peptide allows modification of a peptide sequence compared to a system using a cationic lipid or polyethyleneimine (PEI) and thus it enables delivery to subdomains within cells at various sites and delivery of various types of materials to be delivered into cells.

Accordingly, the present inventors have developed a novel cell-penetrating peptide that has excellent skin improvement effect as well as cell penetration effect, and confirmed that the novel peptide and peptide-active ingredient complex show various skin improvement effects such as cell penetration, skin whitening, wrinkle improvement, antioxidation, antiaging, atopy alleviation, hair loss prevention and hair growth promotion.

SUMMARY

The present disclosure provides a novel cell-penetrating multifunctional peptide, a composition for drug delivery and a cosmetic composition for skin improvement including the same.

However, problems to be solved by the present disclosure are not limited to the above-described problems. Although not described herein, other problems to be solved by the present disclosure can be clearly understood by those skilled in the art from the following descriptions.

A first aspect of the present disclosure provides a cell-penetrating multifunctional peptide, including an amino acid sequence of SEQ ID NO: 1.

A second aspect of the present disclosure provides a composition for drug delivery, including the cell-penetrating multifunctional peptide of the present disclosure; and a target drug.

A third aspect of the present disclosure provides a cosmetic composition for skin improvement, including the cell-penetrating multifunctional peptide of the present disclosure.

A fourth aspect of the present disclosure provides a cosmetic composition for skin improvement, including the cell-penetrating multifunctional peptide of the present disclosure; and a drug.

A fifth aspect of the present disclosure provides a pharmaceutical composition for skin improvement, including the cell-penetrating multifunctional peptide of the present disclosure, or including the cell-penetrating multifunctional peptide of the present disclosure; and a drug.

Since a novel cell-penetrating multifunctional peptide according to the embodiments of the present disclosure have cell penetrability or skin penetrability, the cell-penetrating multifunctional peptide itself or a drug conjugated to the peptide can be very effectively delivered into cells or skin. Also, the cell-penetrating multifunctional peptide enables the drug to more remarkably exhibit its own functions, such as increase in cell growth or promotion of collagen synthesis.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

FIG. 3B shows the result of checking cell proliferation of HDF-N (human dermal fibroblast-neonatal) cells treated with various concentrations of Spep001 (SEQ ID NO: 1), Spep002 (SEQ ID NO: 8) or Spep003 (SEQ ID NO: 1) by a WST-1 assay according to an example of the present disclosure.

FIG. 8A(i) to FIG. 8A(xii) and FIG. 8B show microscopic images of the appearance of HDF-N cells treated with various concentrations of KTTKS (SEQ ID NO: 5), KTTKS-Spep001 (SEQ ID NO: 7) or Spep001-KTTKS (SEQ ID NO: 6) (FIG. 8A(i) to FIG. 8A(xii)) and also shows the result of checking the cell proliferation rate by a WST-1 assay (FIG. 8B) according to an example of the present disclosure.

DETAILED DESCRIPTION

Figure 1A:
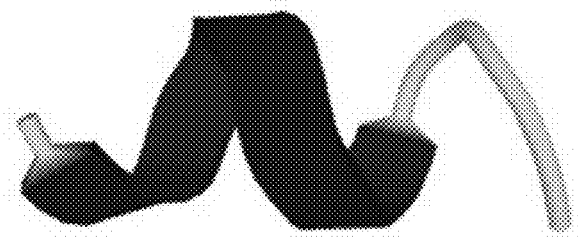
FIG. 1A(i) to FIG. 1A(iii) show the result of analysis of the 3D structures of cell-penetrating multifunctional peptides Spep001 (SEQ ID NO: 1), Spep002 (SEQ ID NO: 8) and Spep003 (SEQ ID NO: 9) according to an example of the present disclosure.
Figure 1A:
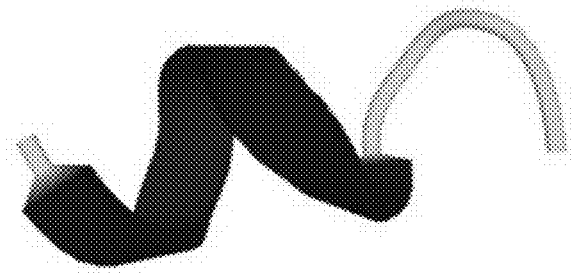
Figure 1A:
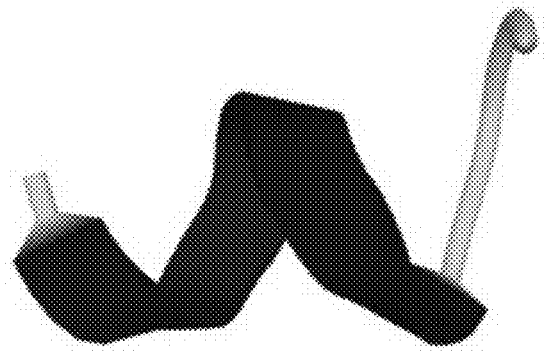

Hereafter, embodiments of the present disclosure will be described in detail with reference to the accompanying drawings. However, it is to be noted that the present disclosure is not limited to the embodiments but can be embodied in various other ways. Also, the accompanying drawings are provided to help easily understand the embodiments of the present disclosure and the technical conception described in the present disclosure is not limited by the accompanying drawings. In the drawings, parts irrelevant to the description are omitted for the simplicity of explanation, and the size, form and shape of each component illustrated in the drawings can be modified in various ways. Like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through this whole specification, a phrase in the form "A and/or B" means "A or B, or A and B".

A first aspect of the present disclosure provides a cell-penetrating multifunctional peptide, including an amino acid sequence of SEQ ID NO: 1.

In an embodiment of the present disclosure, the cell-penetrating multifunctional peptide may be a cell-penetrating or skin-penetrating peptide.

In an embodiment of the present disclosure, the cell-penetrating multifunctional peptide has cell-penetrating ability or skin-penetrating ability and thus can transport or deliver various active ingredients such as low-molecular substances and also, the cell-penetrating multifunctional peptide itself is effective in skin improvement (skin moisturizing, skin whitening, skin elasticity improvement, skin reproduction or wrinkle improvement). Further, the cell-penetrating multifunctional peptide is highly useful for drugs, preparations for skin external application or cosmetics.

Through the whole document, the term "cell penetrability" refers to the ability or property of a peptide to penetrate into cells through cell membrane.

Through the whole document, the term "skin penetrability" refers to the ability or property of a peptide that penetrates skin regardless of molecular size or property thereof, uniformly spreads throughout the skin and has excellent skin penetrability and excellent skin retentivity.

In an embodiment of the present disclosure, the cell-penetrating multifunctional peptide may be derived from N-acetylgalactosamine-4-O-sulfotransferase, but is not limited thereto.

In an embodiment of the present disclosure, the cell-penetrating multifunctional peptide may include 10 to 30 amino acid sequences, and specifically, the cell-penetrating multifunctional peptide may include an amino acid sequence of SEQ ID NO: 1 that is repeated twice, three times, five times, seven times or ten times, but is not limited thereto.

In an embodiment of the present disclosure, the amino acid sequence of SEQ ID NO: 1 may be repeated twice or more, but is not limited thereto.

In an embodiment of the present disclosure, the cell-penetrating multifunctional peptide may be encoded with any one of nucleotides of SEQ ID NOs: 2 to 4, but is not limited thereto.

In an embodiment of the present disclosure, an amino acid including the amino acid sequence of SEQ ID NO: 1 may have a homology or identity of at least 80%, 85%, 90%, 95%, 96%, 97%, 98%, 99% or 100% with the amino acid sequence of SEQ ID NO: 1 of the present disclosure, but is not limited thereto.

In an embodiment of the present disclosure, the term "homology" or "identity" refers to the degree of relevance between two amino acid sequences and may be expressed as a percentage. The terms "homology" and "identity" may be interchangeably used with each other.

In an embodiment of the present disclosure, the cell-penetrating multifunctional peptide may be prepared by a chemical peptide synthesis known in the art, such as solid phase peptide synthesis (SPPS), or may be prepared by amplifying a gene that encodes the peptide through a polymerase chain reaction (PCR) or synthesizing the gene by a known method and then cloning in an expression vector to be expressed, but is not limited thereto. In an embodiment of the present disclosure, the cell-penetrating multifunctional peptide may refer to a peptide prepared using cells or an artificially synthesized peptide, but is not limited thereto. For example, the peptide may be obtained as a recombinant by incorporating a DNA encoding the peptide into an appropriate expression system, or may be synthesized artificially, but is not limited thereto.

In an embodiment of the present disclosure, the cell-penetrating multifunctional peptide may be prepared using a human-derived peptide, a non-human-derived peptide or a viral peptide, but is not limited thereto.

In an embodiment of the present disclosure, the cell-penetrating multifunctional peptide may further include a part or all of a sequence derived from a conventionally known cell-penetrating peptide or skin-penetrating peptide, but is not limited thereto. For example, the conventionally known cell-penetrating peptide is not limited as long as it has cell-penetrating activity. Specifically, the conventionally known cell-penetrating peptide may be selected from the group consisting of dNP2, Penetratin, TAT, Transpotan, MAP, KALA, P1, MPG, Pep-1, Arg(7,9,11), hCT, pVEC, SPEH, YARA, WLR, VP22, MTS, FHV coat and combinations thereof, but is not limited thereto.

In an embodiment of the present disclosure, the cell-penetrating multifunctional peptide may be used as a pharmaceutical composition, a cosmetic composition, a preparation composition for skin external application and/or a food composition for skin improvement, but is not limited thereto.

In an embodiment of the present disclosure, the skin improvement may be at least one selected from the group consisting of skin moisturizing, skin whitening, skin elasticity improvement, skin reproduction or wrinkle improvement, but is not limited thereto.

A second aspect of the present disclosure provides a composition for drug delivery, including the cell-penetrating multifunctional peptide of the present disclosure; and a target drug.

Detailed descriptions on the composition for drug delivery according to the second aspect of the present disclosure, which overlap with those on the first aspect of the present disclosure, are omitted hereinafter, but the descriptions of the first aspect of the present disclosure may be identically applied to the second aspect of the present disclosure, even though they are omitted hereinafter.

In an embodiment of the present disclosure, the composition may be a composition for intradermal, percutaneous or intracellular drug delivery.

In an embodiment of the present disclosure, the composition may be a cell penetration enhancing composition or a skin penetration enhancing composition.

In an embodiment of the present disclosure, the composition may be used for enhancing the cell penetrability or skin penetrability of the drug or for delivering the drug into cells or skin.

In an embodiment of the present disclosure, the drug may be a compound, a protein or a nucleic acid. The compound may be at least one selected from the group consisting of fat, carbohydrate, dye, photosensitizer, anticancer drug, antibiotic and low-molecular compound, but is not limited thereto. The protein may be at least one selected from the group consisting of enzyme, ligand, hormone, carrier, immunoglobulin, antibody, structural protein, motor functioning peptide, receptor, signaling peptide, storing peptide, membrane peptide, transmembrane peptide, internal peptide, external peptide, secreting peptide, virus peptide, native peptide, glycated protein, fragmented protein, disulfide bonded protein, recombinant protein and chemically modified protein, but is not limited thereto. The nucleic acid may be at least one selected from the group consisting of coding nucleic acid sequence, mRNA, siRNA, microRNA, plasmid, gene, antisense RNA and oligonucleotide, but is not limited thereto.

In an embodiment of the present disclosure, the drug may be linked to the N-terminus or C-terminus of the cell-penetrating multifunctional peptide, but is not limited thereto as long as it can enhance cell penetrability or skin penetrability without inhibiting pharmacological activity of the drug.

In an embodiment of the present disclosure, the drug may be linked to the cell-penetrating multifunctional peptide through a linker or may be directly linked to the cell-penetrating multifunctional peptide. The linker is not particularly limited as long as it can enhance the activity of a conjugate in which the drug is conjugated to the cell-penetrating multifunctional peptide. For example, if a compound is used as the drug, the linker may be a compound capable of promoting conjugation of the drug; or if a protein or a nucleic acid is used as the drug, the linker may be a peptide capable of promoting conjugation of the drug.

In an embodiment of the present disclosure, the linker may be cleaved or degraded by various biological and chemical actions such as enzyme actions in cells or skin. As the linker is cleaved or degraded, the cell-penetrating multifunctional peptide and the drug may be separated from each other in targeted cells or skin. An amino acid sequence that can be cleaved by an enzyme, which is overexpressed in targeted tissue or cells where the cell-penetrating multifunctional peptide is to be located, may be included as the linker. The conjugation linker of the present disclosure may be, for example, a peptide conjugation linker composed of 33 amino acids at positions 282 to 314 or a peptide conjugation linker composed of 13 amino acids at positions 292 to 304 in human albumin, which is the most abundant in blood, but is not limited thereto.

In an embodiment of the present disclosure, the drug may form a conjugate or complex by mutual coupling with the cell-penetrating multifunctional peptide or may be mixed with the cell-penetrating multifunctional peptide without mutual coupling to form a noncovalent conjugate, but is not limited thereto as long as it can enhance cell penetrability or skin penetrability without inhibiting pharmacological activity of the drug.

In an embodiment of the present disclosure, the drug cannot be naturally introduced into cells or skin, or cannot be naturally introduced into cells or skin at a useful speed, but is not limited thereto.

In an embodiment of the present disclosure, the composition in which the cell-penetrating multifunctional peptide and the drug are chemically or physically linked to each other, for example, covalently or noncovalently bonded to each other may be quickly and safely penetrated into cells through an in vivo or in vitro process. For example, the composition in which the cell-penetrating multifunctional peptide and the drug are linked may be introduced into cells through endocytosis, which is a conventional intracellular absorption method, or may be directly introduced into cells without such a process.

A third aspect of the present disclosure provides a cosmetic composition for skin improvement, including the cell-penetrating multifunctional peptide of the present disclosure.

Detailed descriptions on the cosmetic composition according to the third aspect of the present disclosure, which overlap with those on the first aspect or the second aspect of the present disclosure, are omitted hereinafter, but the descriptions of the first aspect or the second aspect of the present disclosure may be identically applied to the third aspect of the present disclosure, even though they are omitted hereinafter.

In an embodiment of the present disclosure, the skin improvement may be at least one selected from the group consisting of skin moisturizing, skin whitening, skin elasticity improvement, skin reproduction or wrinkle improvement, but is not limited thereto.

In an embodiment of the present disclosure, the cosmetic composition may include the cell-penetrating multifunctional peptide linked to a drug, for example, an effective peptide, KTTKS (SEQ ID NO: 5) linked to the N-terminus or C-terminus of the peptide, and may be directly linked or linked through a linker, but is not limited thereto.

In an embodiment of the present disclosure, the formulation of the cosmetic composition is not particularly limited, and the cosmetic composition may be prepared into a formulation selected from, for example, toners, lotions, essences, creams, packs, foundations, patches, hair tonics, micro-needle patches and make-up bases, but is not limited thereto.

In an embodiment of the present disclosure, the cosmetic composition may further include any material selected suitable for the formulation or use purpose of cosmetics, and may include, for example, purified water, oils, surfactants, moisturizing agents, higher alcohols, thickeners, chelating agents, pigments, fatty acids, antioxidants, preservatives, waxes, pH regulators, fragrances and the like, but is not limited thereto.

In an embodiment of the present disclosure, if the formulation of the cosmetic composition is paste, cream or gel, the cosmetic composition may include animal and vegetable oils, waxes, paraffins, starch, tragacanth, cellulose derivatives, polyethylene glycols, silicones, bentonites, silica, talc or zinc oxide as a carrier, but is not limited thereto.

In an embodiment of the present disclosure, if the formulation of the cosmetic composition is powder or spray, the cosmetic composition may include lactose, talc, silica, aluminum hydroxide, calcium silicates or polyamide powder as a carrier, and particularly, in the case of spray, it may further include a propellant such as chlorofluorohydrocarbon, propane/butane or dimethyl ester, but is not limited thereto.

In an embodiment of the present disclosure, if the formulation of the cosmetic composition is a solution or an emulsion, the cosmetic composition may include solvents, solvating agents or emulsifying agents as a carrier, and may include, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol or sorbitan fatty acid ester, but is not limited thereto.

In an embodiment of the present disclosure, if the formulation of the cosmetic composition is a suspension, the cosmetic composition may include liquid diluting agents, such as water, ethanol or propylene glycol, suspending agents, such as ethoxylated isostearyl alcohol, polyoxyethylene sorbitol ester and polyoxyethylene sorbitan ester, microcrystalline cellulose, aluminum meta-hydroxide, bentonite, agar or tragacanth, etc. as a carrier, but is not limited thereto.

In an embodiment of the present disclosure, if the formulation of the cosmetic composition is a surfactant-containing cleansing composition, the cosmetic composition may include aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betaine, aliphatic alcohol, fatty acid glyceride, fatty acid diethanolamide, vegetable oils, lanoline derivatives or ethoxylated glycerol fatty acid ester as a carrier, but is not limited thereto.

A fourth aspect of the present disclosure provides a cosmetic composition for skin improvement, including the cell-penetrating multifunctional peptide of the present disclosure; and a drug.

Detailed descriptions on the cosmetic composition according to the fourth aspect of the present disclosure, which overlap with those on the first aspect to the third aspect of the present disclosure, are omitted hereinafter, but the descriptions of the first aspect to the third aspect of the present disclosure may be identically applied to the fourth aspect of the present disclosure, even though they are omitted hereinafter.

A fifth aspect of the present disclosure provides a pharmaceutical composition for skin improvement, including the cell-penetrating multifunctional peptide of the present disclosure, or including the cell-penetrating multifunctional peptide of the present disclosure; and a drug.

Detailed descriptions on the pharmaceutical composition according to the fifth aspect of the present disclosure, which overlap with those on the first aspect to the third aspect of the present disclosure, are omitted hereinafter, but the descriptions of the first aspect to the third aspect of the present disclosure may be identically applied to the fifth aspect of the present disclosure, even though they are omitted hereinafter.

In an embodiment of the present disclosure, the pharmaceutical composition may be formulated and used as formulations for oral administration such as powders, granules, tablets, capsules, suspensions, emulsions, syrups or aerosol, external preparations, suppositories or sterile injection solutions by conventional methods, respectively, but is not limited thereto.

In an embodiment of the present disclosure, the pharmaceutical composition may be formulated with generally used diluents or excipients such as fillers, extenders, binders, wetting agents, disintegrating agents or surfactants, but is not limited thereto.

In an embodiment of the present disclosure, solid formulations for oral administration may include tablets, pills, powders, granules or capsules, and these solid formulations may be prepared by mixing at least one of excipients such as starch, calcium carbonate, sucrose, lactose, glucose, malto-dextrin or gelatin. Except for the simple excipients, lubricants such as magnesium stearate or talc may be used, but the present disclosure is not limited thereto.

In an embodiment of the present disclosure, liquid formulations for oral administration may include suspensions, solutions for internal use, emulsions and syrups, and may contain various excipients such as wetting agents, sweeteners, aromatics and preservatives in addition to generally used simple diluents such as water and liquid paraffin, but the present disclosure is not limited thereto.

The pharmaceutical composition according to an embodiment of the present disclosure may be a drug composition or a quasi-drug composition.

Through the whole document, the term "quasi-drug" refers to products that are less effective than pharmaceuticals, among products used for diagnosing, curing, improving, alleviating, treating, or preventing diseases of humans or animals. For example, according to the Pharmaceutical Affairs Law, quasi-drugs exclude products used as pharmaceuticals, and include products used for curing or preventing diseases of humans and animals, products which minimally act on the human body or do not act directly on the human skin, and the like.

The quasi-drug composition of the present disclosure may be prepared in a formulation selected from the group consisting of body cleanser, sanitizer, detergent, kitchen cleanser, detergent for cleaning, toothpaste, mouthwash, wet wipe, cleanser, soap, hand soap, hair cleanser, hair softener, humidifying filler, mask, ointment or filter filler, but is not limited thereto.

The pharmaceutical composition according to an embodiment of the present disclosure may be a preparation composition for skin external application.

Through the whole document, the term "preparation for external application" refers to any preparations externally administered, and may include powders for external application, tablets for external application, liquids for external application, ointments, plaster preparations and suppositories, but is not limited thereto.

The preparation for skin external application according to an embodiment of the present disclosure may be a preparation for parenteral administration, which is formulated in solid, semi-solid or liquid form by adding a compatible inorganic or organic carrier, excipient and diluent. The preparation for parenteral administration may be a transdermal dosage form selected from the group consisting of drops, ointments, lotions, gels, creams, patches, sprays, suspensions and emulsions, but is not limited thereto.

Examples of carriers, excipients and diluents that may be contained in the preparation for external application according to an embodiment of the present disclosure may include lactose, dextrose, sucrose, oligosaccharides, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil, but are not limited thereto.

In the preparation composition for skin external application according to each formulation, components other than the composition of the present disclosure may be appropriately selected and mixed by a person with ordinary skill in the art without difficulty depending on the formulations or use purposes of other preparations for skin external application, and in this case, a synergistic effect may be obtained when applied simultaneously with other raw materials.

Hereinafter, example embodiments are described in more detail by using Examples, but the present disclosure may not limited to the Examples.

EXAMPLES

<Example 1> Design and Selection of Novel Cell-Penetrating Multifunctional Peptide To select a cell-penetrating multifunctional peptide, the level of a cell-penetrating peptide (CPP) having a peptide sequence derived from a membrane protein described in a prior art document was screened, and the result thereof is shown in Table 1 below.

Herein, TAT (SEQ ID NO: 10) has a CPP score of 1.84.

The CPP score refers to the degree of cell penetrability.

Referring to the CPP scores in Table 1, Spep001 (SEQ ID NO: 1) as a control has a CPP score of 1.89, which is higher by about 0.05 than that of TAT (SEQ ID NO: 10). Further, Spep002 (SEQ ID NO: 8) and Spep003 (SEQ ID NO: 9) have CPP scores of 1.71 and 1.65, respectively.

The peptides whose CPP scores were confirmed were synthesized by SPPS, and the purities of the finally synthesized peptides are as shown in Table 1 below.

TABLE 1

| CPP | Origin | Sequence | CPP score | MW | Purity |
|---|---|---|---|---|---|
| TAT (SEQ ID NO: 10) | Human immunodeficiency virus 1 | YGRKRRQRRR | 1.84 | 1560.36 | 99.53% |

TABLE 1-continued

| CPP | Origin | Sequence | CPP score | MW | Purity |
|---|---|---|---|---|---|
| Spep001 (SEQ ID NO: 1) | N-acetylgalactosamine-4-O-sulfotransferase | RLRLRQRRRR | 1.89 | 1466.37 | 95.11% |
| Spep002 (SEQ ID NO: 8) | Muscarinic acetylcholine receptor M1 | KRRWRKIPKR | 1.71 | 1424.33 | 98.23% |
| Spep003 (SEQ ID NO: 9) | TFIIIC box B-binding subunit | RKRWLRKPRP | 1.65 | 1393.24 | 97.97% |

<Example 2> Confirmation of Structure of Cell-Penetrating Multifunctional Peptide The 3D structure of the penetrating multifunctional peptide according to Example 1 was analyzed by using PEP-FOLD 3.5 from RPBS Web Portal, and the helical wheel of the penetrating multifunctional peptide according to Example 1 was predicted by using Pepwheel. The results thereof are shown in FIG. 1A(i) to FIG. 1(iii) and FIG. 1B(i) to FIG. 1B(iii).

Figure 1B:
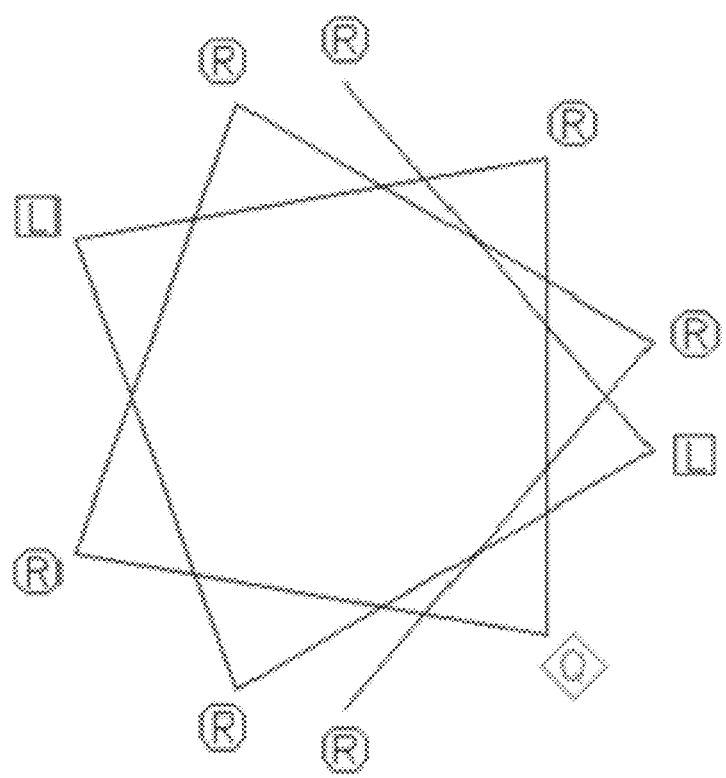
FIG. 1B(i) to FIG. 1B(iii) show the result of analysis of the helical wheels of cell-penetrating multifunctional peptides Spep001 (SEQ ID NO: 1), Spep002 (SEQ ID NO: 8) and Spep003 (SEQ ID NO: 9) according to an example of the present disclosure.

Referring to the 3D structure and the helical wheel shown in FIG. 1A(i) to FIG. 1A(iii) and FIG. 1B(i) to FIG. 1B(iii), all of Spep001(SEQ ID NO: 1), Spep002 (SEQ ID NO: 8) and Spep003 (SEQ ID NO: 9) have helical wheel structures.

<Example 3> Cytotoxictiy Assay of Cell-Penetrating Multifunctional Peptide (1)

Cytotoxicity of the cell-penetrating multifunctional peptide according to Example 1 was checked. Specifically, HaCaT cells (human keratinocytes) were inoculated at a concentration of $1.5 \times 10^4$ cells/well into a 96-well plate and incubated for 24 hours. Then, the medium was removed, followed by washing once with PBS, and replaced with a serum-free medium. The cells were treated with Spep001 (SEQ ID NO: 1), Spep002 (SEQ ID NO: 8) or Spep003 (SEQ ID NO: 9) at a concentration of 0 μM, 25 μM, 50 μM, 100 μM or 200 μM and then further incubated for 24 hours. Herein, culture conditions were maintained at 37° C. with 5% $CO_2$.

Figure 2A:
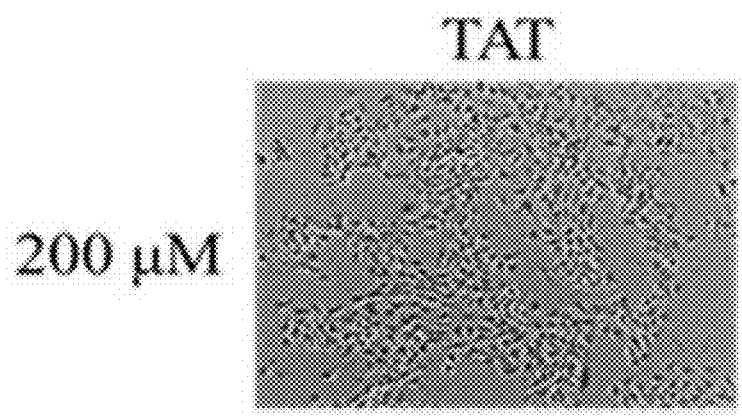
FIG. 2A(i) to FIG. 2A(xx) show microscopic images of the appearance of HaCaT cells (human keratinocytes) treated with various concentrations of Spep001 (SEQ ID NO: 1), Spep002 (SEQ ID NO: 8) or Spep003 (SEQ ID NO: 9) according to an example of the present disclosure.
Figure 2A:
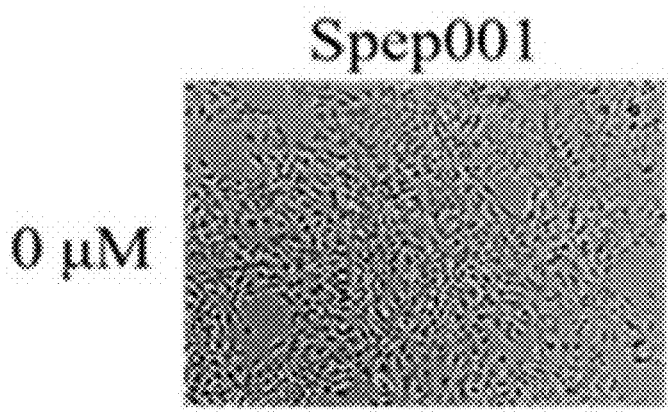
Figure 2A:
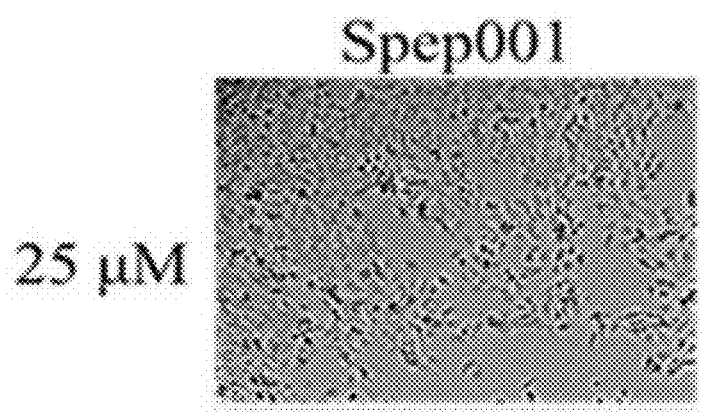

At the time of completion of further incubation, the appearance of the cells were imaged by a microscope, and the result thereof is shown in FIG. 2A(i) to FIG. 2A(xx).

Figure 2B:
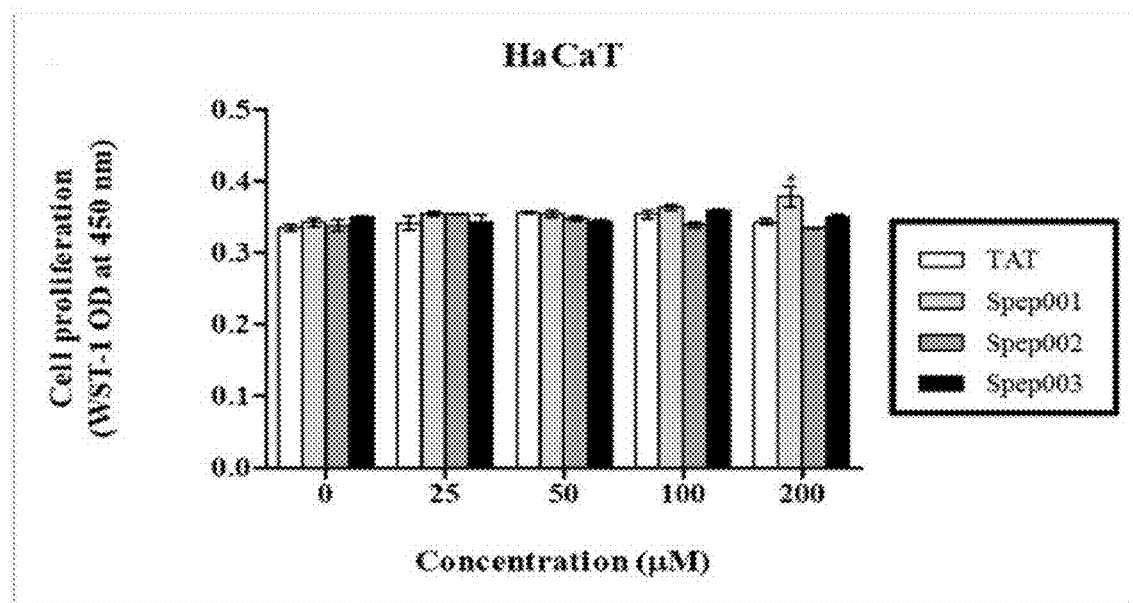
FIG. 2B shows the result of checking cell proliferation of HaCaT cells (human keratinocytes) treated with various concentrations of Spep001 (SEQ ID NO: 1), Spep002 (SEQ ID NO: 8) or Spep003 (SEQ ID NO: 9) by a WST-1 assay according to an example of the present disclosure.

Also, at the time of completion of incubation, a WST-1 assay (Water Soluble Tetrazolium salt-1, EZ-assay kit, DoGenBio) was conducted. Specifically, 100 μL of a WST-1 solution was added to the well of cells after the completion of further incubation and then incubated for 3 hours. Thereafter, the absorbance at 450 nm was measured using a microplate spectrophotometer (Multiskan™ GO, thermo), and the result thereof is shown in FIG. 2B and Table 2 below.

Herein, all the result values are expressed in mean±standard deviation. The analysis result of each item was statistically analyzed by a 2-way analysis of variance (ANOVA) test. A Bonferroni post-test was conducted at a P value of $*p<0.05$ and $**p<0.01$ only when the significance was determined by ANOVA test. GraphPad prism 5.0.1 (GraphPad Software Inc., San Diego, CA, USA) was used as a statistical software program.

TABLE 2

| | HaCaT | | | | |
|---|---|---|---|---|---|
| | Peptide Concentration (μM) | | | | |
| Treatment | 0 | 25 | 50 | 100 | 200 |
| TAT (SEQ ID NO: 10) | 100 ± 2.71 | 101.99 ± 5.09 | 106.27 ± 1.05 | 105.68 ± 2.94 | 102.49 ± 2.15 |
| Spep001 (SEQ ID NO: 1) | 100 ± 2.86 | 103.31 ± 1.62 | 103.40 ± 2.21 | 106.03 ± 2.23 | 110.31 ± 7.48 |
| Spep002 (SEQ ID NO: 8) | 100 ± 4.15 | 104.74 ± 0.17 | 102.96 ± 1.97 | 100.59 ± 1.97 | 99.01 ± 0.62 |
| Spep003 (SEQ ID NO: 9) | 100 ± 0.83 | 98.28 ± 4.45 | 98.57 ± 1.01 | 102.96 ± 0.60 | 99.91 ± 1.79 |

Referring to the images of the appearance of the cells shown in FIG. 2A(i) to FIG. 2A(xx), it was confirmed that there was no change in the appearance of the HaCaT cells treated with Spep001 (SEQ ID NO: 1), Spep002 (SEQ ID NO: 8) or Spep003 (SEQ ID NO: 9) at all concentrations.

Also, as can be seen from the survival rate values in FIG. 2B and Table 2, the survival rates of the HaCaT cells treated with Spep001(SEQ ID NO: 1), Spep002 (SEQ ID NO: 8) or Spep003(SEQ ID NO: 9) were 90% or more at all concentrations.

According to the above results, it can be seen that all of Spep001 (SEQ ID NO: 1), Spep002(SEQ ID NO: 8) and Spep003 (SEQ ID NO: 9) do not express cytotoxicity in the HaCaT cells.

<Example 4> Cytotoxictiy Assay of Cell-Penetrating Multifunctional Peptide (2)

Figure 3A:
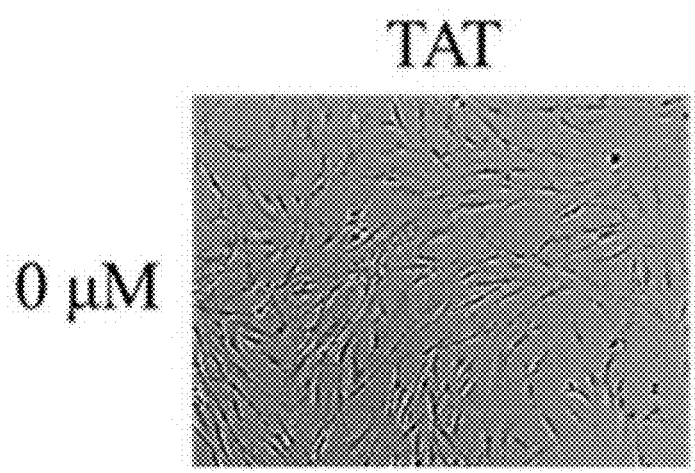
FIG. 3A(i) to FIG. 3A(xx) show microscopic images of the appearance of HDF-N (human dermal fibroblast-neonatal) cells treated with various concentrations of Spep001 (SEQ ID NO: 1), Spep002 (SEQ ID NO: 8) or Spep003 (SEQ ID NO: 1) according to an example of the present disclosure.
Figure 3A:
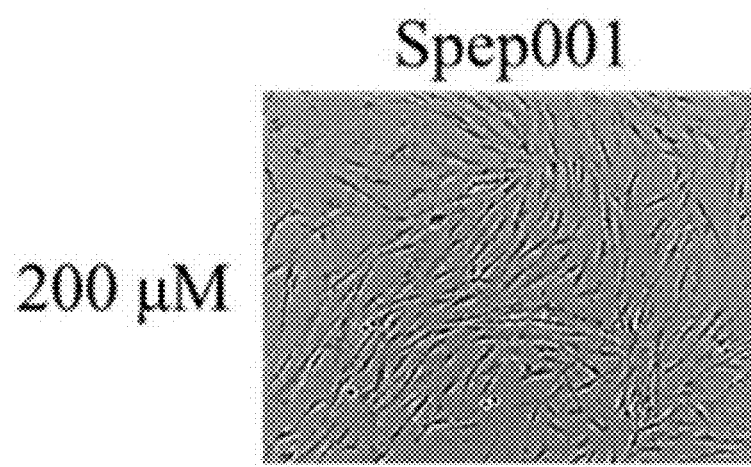
Figure 3A:
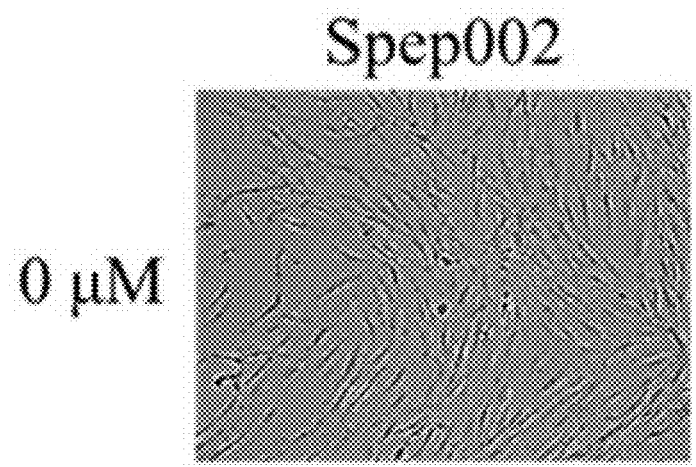

The appearance of HDF-N (human dermal fibroblast-neonatal) cells were imaged by a microscope as in Example 3, and the result thereof is shown in FIG. 3A(i) to FIG. 3A(xx). Also, cell proliferation was checked by a WST-1 assay, and the result thereof is shown in FIG. 3B. However, the HDF-N cells were inoculated at a concentration of $1.0 \times 10^4$ cells/well into a 96-well plate.

Referring to the images of the appearance of the cells shown in FIG. 3A(i) to FIG. 3A(xx), it was confirmed that there was no change in the appearance of the HDF-N cells treated with Spep001 (SEQ ID NO: 1), Spep002 (SEQ ID NO: 8) or Spep003 (SEQ ID NO: 9) at all concentrations.

FITC (Fluorescein-5-Isothiocyanate), which is a fluorescent material, to the amine groups at the N-termini of cell-penetrating multifunctional peptides corresponding to Spep001 (SEQ ID NO: 1), Spep002 (SEQ ID NO: 8) and Spep003 (SEQ ID NO: 9).

The molecular weights and purities of the fabricated fluorescence-labelled cell-penetrating multifunctional peptides are as shown in Table 4 below.

TABLE 4

| FITC-CPPs | Sequences | MW | Purity |
|---|---|---|---|
| FITC-Ahx-Spep001 | FITC-Ahx-RLRLRQRRRR | 1969.70 | 95.39% |
| FITC-Ahx-Spep002 | FITC-Ahx-KRRWRKIPKR | 1926.55 | 95.19% |
| FITC-Ahx-Spep003 | FITC-Ahx-RKRWLRKPRP | 1895.45 | 95.55% |

HaCaT cells were inoculated at a concentration of $1.5 \times 10^4$ cells/well into an optical 96-well plate (M0562, Greiner) and incubated for 24 hours. Then, the medium was removed, followed by washing once with HBSS, and replaced with a serum-free medium. The cells were treated with 10 μM FITC-Spep001, FITC-Spep002 or FITC-Spep003 and then further incubated for 24 hours. Thereafter, the cells were washed four times with HBSS and treated with 10 μg/mL H33342 (bisBenzimide H33342 trihydrochloride (B2261, Sigma)) and then further incubated at room temperature for 5 minutes. Finally, the cells were washed three times with HBSS. The cell penetration rate was checked using a super

TABLE 3

| | HDF-N | | | | |
|---|---|---|---|---|---|
| | Peptide Concentration (μM) | | | | |
| Treatment | 0 | 25 | 50 | 100 | 200 |
| TAT (SEQ ID NO: 10) | 100 ± 3.92 | 105.87 ± 3.38 | 94.91 ± 4.22 | 102.85 ± 3.02 | 96.68 ± 5.03 |
| Spep001 (SEQ ID NO: 1) | 100 ± 3.39 | 93.39 ± 0.66 | 101.34 ± 2.71 | 94.97 ± 1.53 | 94.46 ± 2.41 |
| Spep002 (SEQ ID NO: 8) | 100 ± 1.36 | 102.03 ± 4.11 | 104.59 ± 0.75 | 107.97 ± 1.66 | 100.77 ± 2.44 |
| Spep003 (SEQ ID NO: 9) | 100 ± 2.33 | 117.61 ± 5.30 | 104.23 ± 1.71 | 107.95 ± 3.07 | 113.49 ± 0.59 |

Also, as can be seen from the survival rate values in FIG. 3B and Table 3, the survival rates of the HDF-N cells treated with Spep001 (SEQ ID NO: 1), Spep002 (SEQ ID NO: 8) or Spep003 (SEQ ID NO: 9) were 90% or more at all concentrations.

According to the above results, it can be seen that all of Spep001 (SEQ ID NO: 1), Spep002 (SEQ ID NO: 8) and Spep003 (SEQ ID NO: 9) do not express cytotoxicity in the HDF-N cells.

Figure 4A:
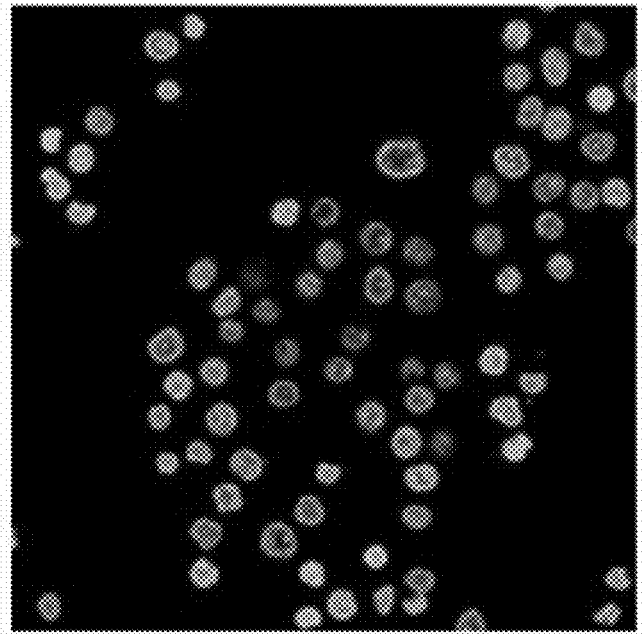
FIG. 4A(i) to FIG. 4A(iv), FIGS. 46(i) to 46(iv), 4C (i) to 4C (iv), 4D (i) to 4D (iv), FIG. 4E(i) to FIG. 4E (iv), and FIG. 4F(i) to FIG. 4F(iv) show the result of checking the cell penetration rate with a fluorescent microscope after treating HaCaT cells with PBS, FITC, FITC-TAT, FITC-Spep001, FITC-Spep002 or FITC-Spep003 according to an example of the present disclosure.
Figure 4A:
Figure 4B:
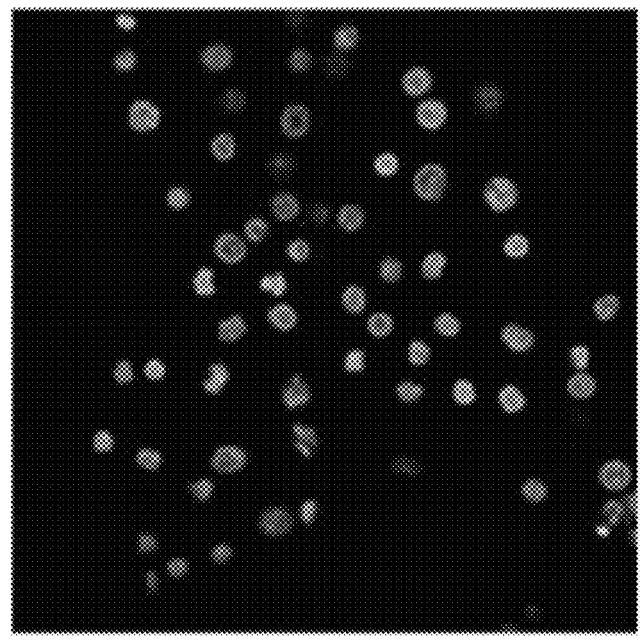
Figure 4C:
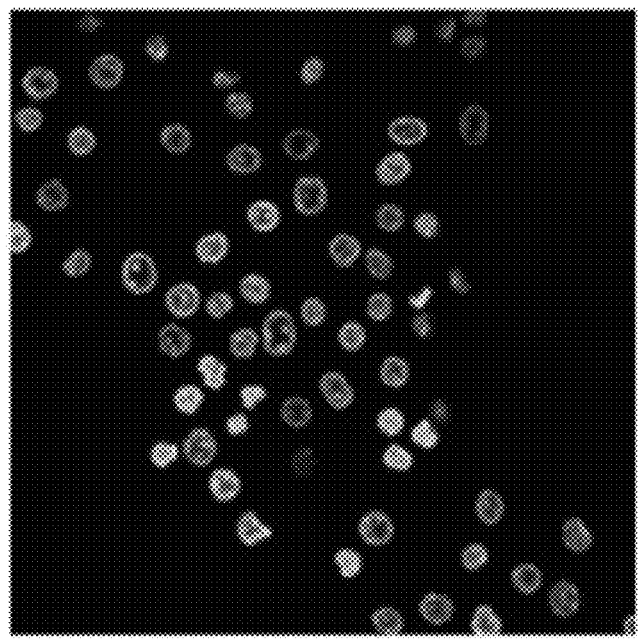
Figure 4E:
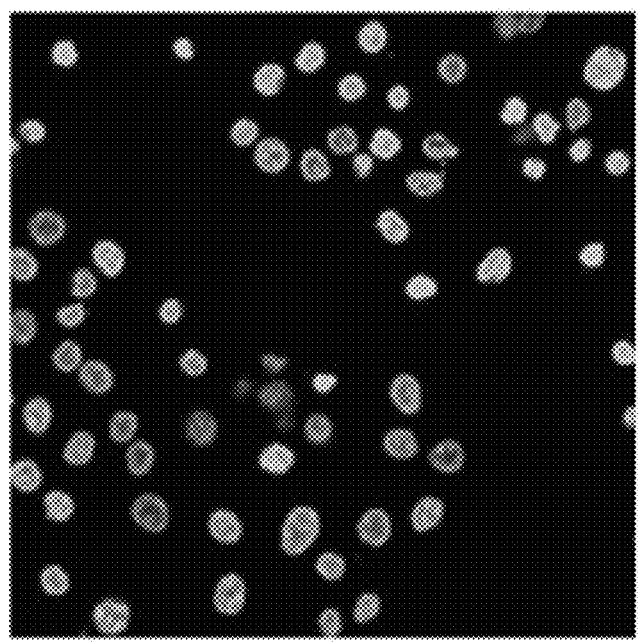

<Example 5> Fabrication of Fluorescence-Labelled Cell-Penetrating Multifunctional Peptide and Evaluation of Penetrability FITC-Ahx-Spep001 (hereinafter, referred to as "FITC-Spep001"), FITC-Ahx-Spep002 (hereinafter, referred to as "FITC-Spep002") and FITC-Ahx-Spep003 (hereinafter, referred to as "FITC-Spep003") were fabricated by labelling resolution confocal laser microscope (LSM800), and the result thereof is shown in FIG. 4A(i) to FIG. 4F(iv). Herein, the cells were treated only FITC (F1906, Invitrogen™) as a negative control, and FITC-TAT was used as a positive control.

Referring to the fluorescent microscopic image shown in FIG. 4A(i) to FIG. 4F(iv), it can be seen that FITC-Spep001 penetrates into cells in a greater amount than the positive control FITC-TAT.

<Example 6> Evaluation on Cell Penetration Rate of Cell-Penetrating Multifunctional Peptide HaCaT cells were inoculated at a concentration of $3 \times 10^5$ cells/well into a 6-well plate and incubated for 24 hours. Then, the cell culture medium was removed, followed by washing twice with HBSS, and replaced with an Opti-MEM medium. The cells were treated with 10 μM FITC-TAT, FITC-Spep001, FITC-Spep002 or FITC-Spep003 and incubated at 37° C. with 5% $CO_2$ for 1 hour. Thereafter, extracellular peptides were removed by washing twice with HBSS and peptides, which did not penetrate into the cells but were attached to the surfaces of the cells, were removed by repeated washing twice with 100 μg/mL heparin. Finally, the cells were treated with 1 mg/mL trypsin and thus separated into single cells, followed by centrifugation at 1,000 rpm for 5 minutes. The FITC fluorescence intensities of cell-penetrating peptides per living 10,000 cells were measured by performing flow cytometry (Navios Flow Cytometer by Beckman Coulter Life Sciences), and the result thereof is shown in FIG. 5A(i) to FIG. 5A(v) and FIG. 5B.

Figure 5A:
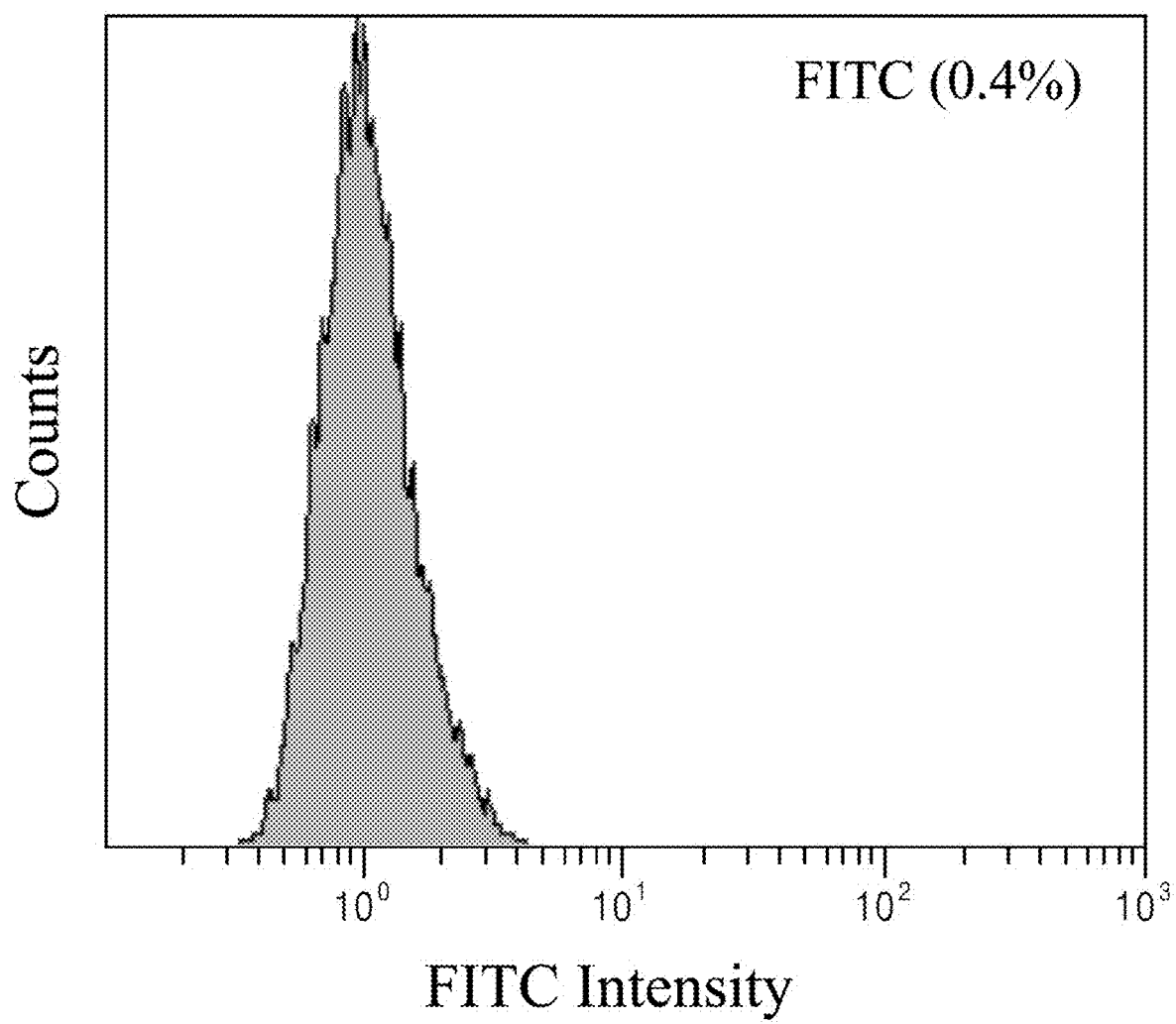
FIG. 5A(i) to FIG. 5A(v) and FIG. 5B show the result of measuring the FITC fluorescence intensities of peptides penetrating into cells by flow cytometry (FIG. 5A(i) to FIG. 5A(v)) and the values of the fluorescence intensities in a graph (FIG. 5B) after treating HaCaT cells with FITC, FITC-TAT, FITC-Spep001, FITC-Spep002 or FITC-Spep003 according to an example of the present disclosure.
Figure 5A:
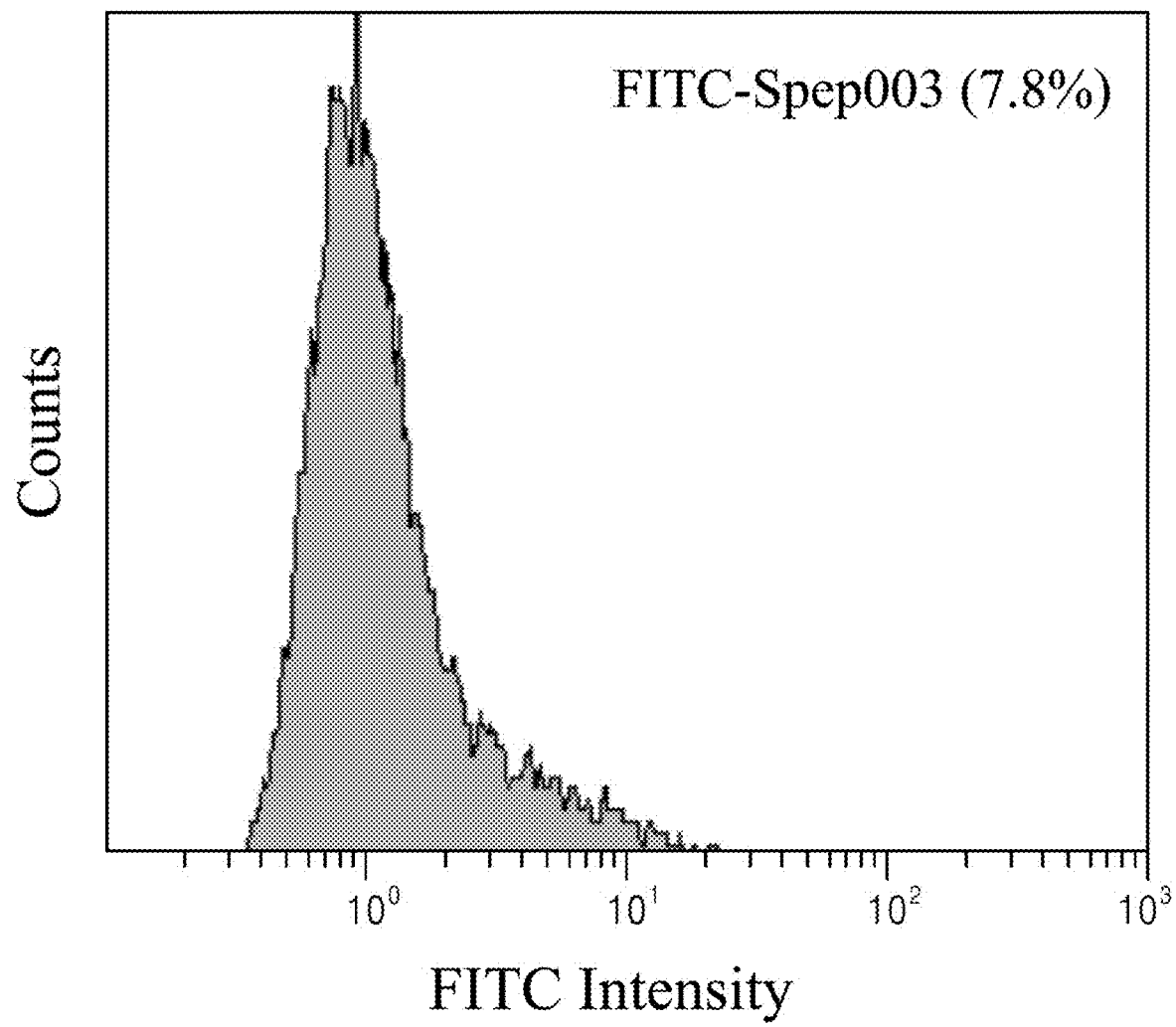
Figure 5B:
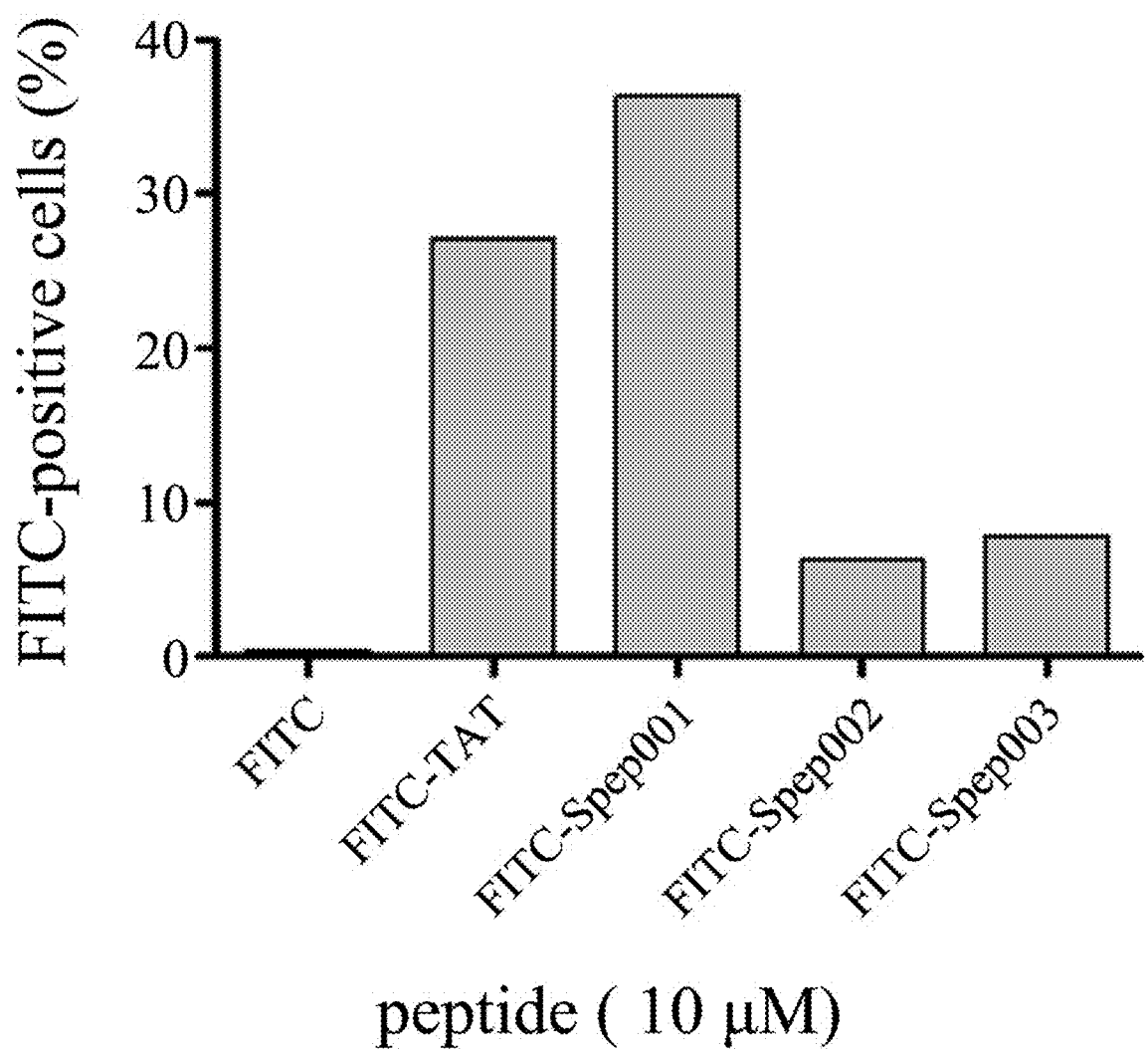

Referring to the FITC-positive cell count (cell penetration rate) shown in FIG. 5A(i) to FIG. 5A(v) and FIG. 5B, the FITC-only treatment group has a cell penetration rate of 0.4%, FITC-Spep001 has a cell penetration rate of 36.3%, FITC-Spep002 has a cell penetration rate of 6.3% and FITC-Spep003 has a cell penetration rate of 7.8% compared to FITC-TAT (27.1%). It can be seen that FITC-Spep001 has a cell penetration rate of 133.95%, FITC-Spep002 has a cell penetration rate of 23.3% and FITC-Spep003 has a cell penetration rate of 28.8% based on TAT-FITC with a cell penetration rate of 100%.

<Example 7> Check of Dependence of Cell-Penetrating Multifunctional Peptide on Temperature A test was conducted in the same conditions as those in Example 6 except that the cells were incubated at a low temperature (4° C.) or 37° C. to check the dependence of endocytosis on temperature. Then, the FITC fluorescence intensities of peptides penetrating into living cells were measured by flow cytometry as in Example 6, and the result thereof is shown in FIG. 6A and FIG. 6B.

Figure 6A:
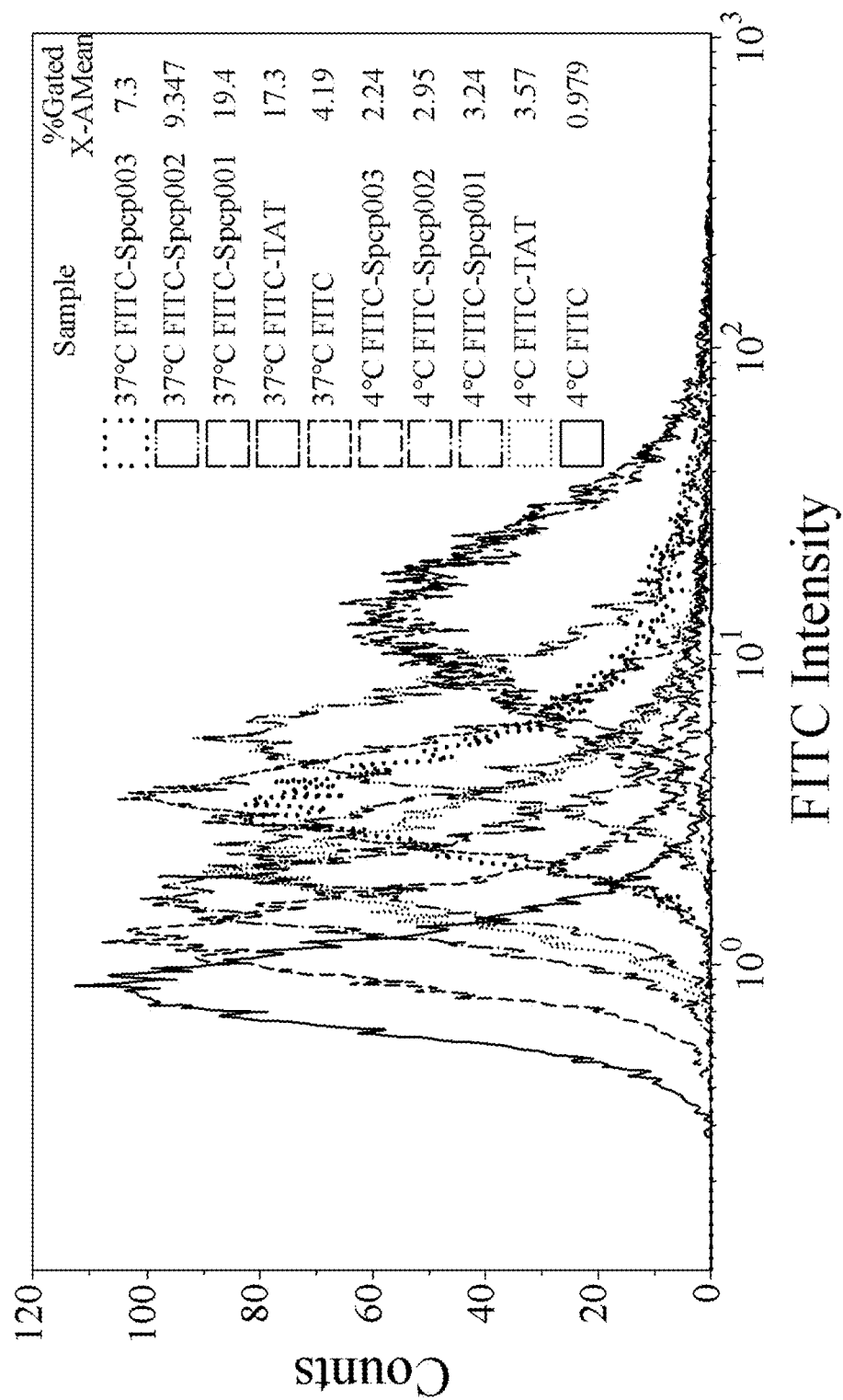
FIG. 6A and FIG. 6B show the result of measuring the FITC fluorescence intensities of peptides penetrating into cells by flow cytometry (FIG. 6A) and the values of the fluorescence intensities in a graph (FIG. 6B) after treating HaCaT cells with FITC, FITC-TAT, FITC-Spep001, FITC-Spep002 or FITC-Spep003 and incubating them at different temperatures of 4° C. or 37° C. according to an example of the present disclosure.
Figure 6B:
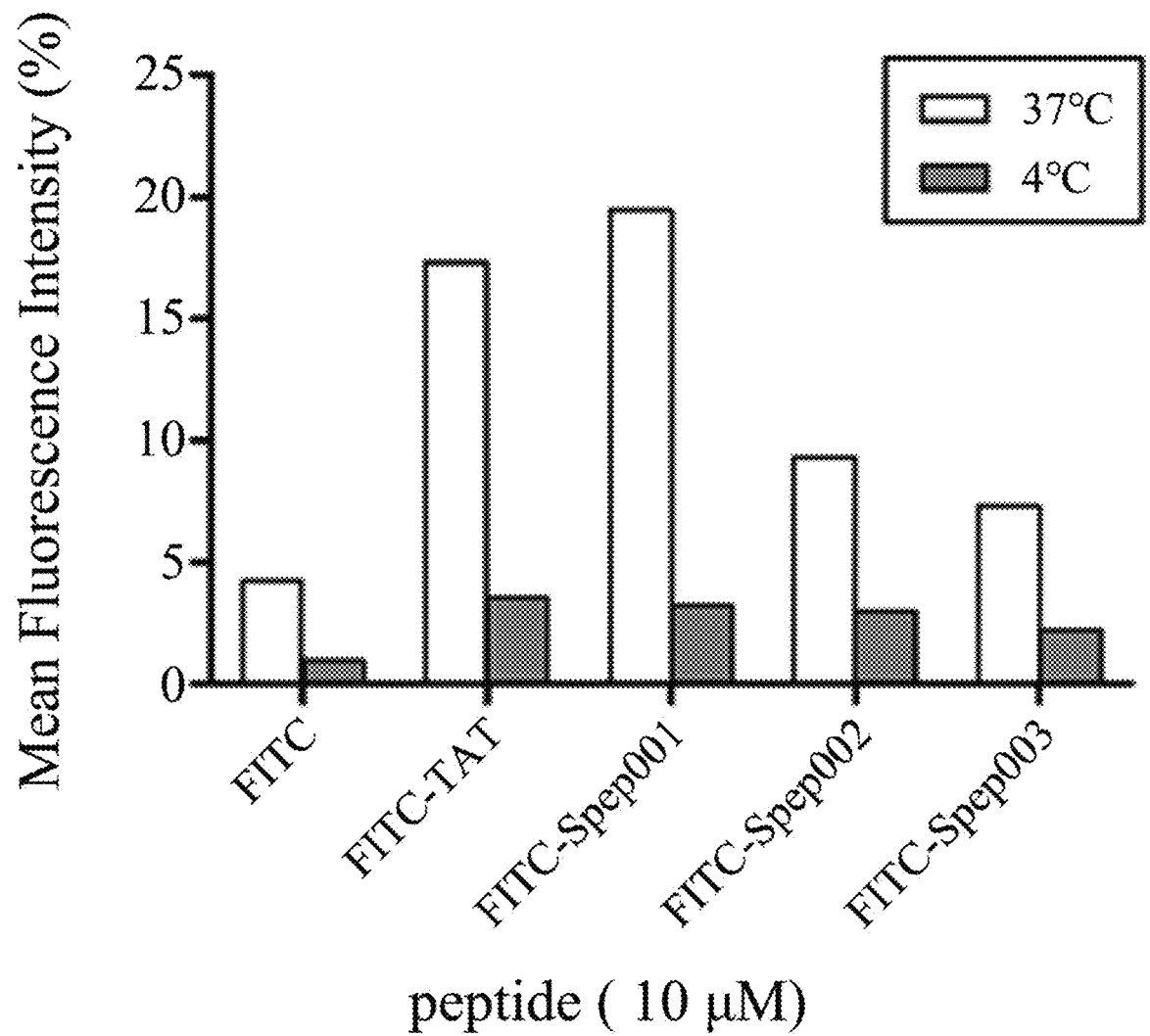

Referring to the fluorescence intensity values shown in FIG. 6A and FIG. 6B, like FITC-TAT, all of FITC-Spep001, FITC-Spep002 and FITC-Spep003 decreased in FITC fluorescence intensity by 80% or more when the incubation temperature was low (4° C.).

According to the above result, it can be seen that the penetration of the cell-penetrating multifunctional peptide of the present disclosure into cells depends on temperature.

<Example 8> Check of Dependence of Cell-Penetrating Multifunctional Peptide on ATP A test was conducted in the same conditions as those in Example 7 except that the cells were pre-treated with 2-DG (2-deoxyglucose, D6134, sigma) and $NaN_3$ (sodium azide, 71289, sigma) one hour before treatment with FITC-TAT, FITC-Spep001, FITC-Spep002 or FITC-Spep003 to check the dependence of endocytosis on ATP. Then, the FITC fluorescence intensities of peptides penetrating into living cells were measured by flow cytometry as in Example 5, and the result thereof is shown in FIG. 7.

Figure 7:
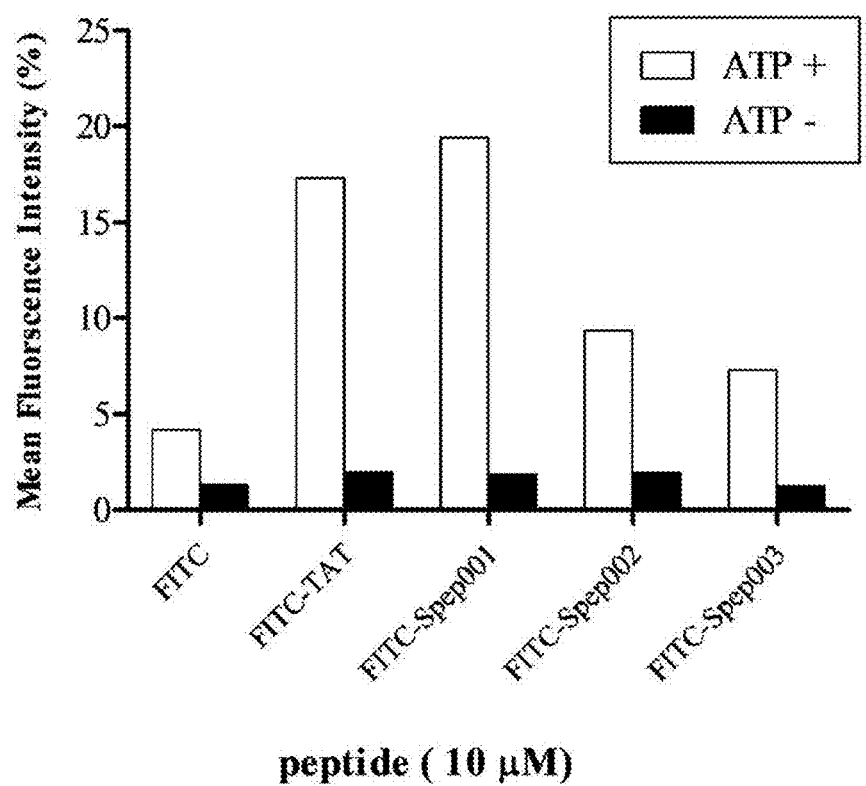
FIG. 7 shows the result of measuring the FITC fluorescence intensities of peptides penetrating into cells by flow cytometry under normal (ATP+) or ATP deficiency (ATP−) condition after treating HaCaT cells with FITC, FITC-TAT, FITC-Spep001, FITC-Spep002 or FITC-Spep003 according to an example of the present disclosure.

Referring to the fluorescence intensity values shown in FIG. 7, when 2-DG and $NaN_3$ were used to cause a deficiency of ATP in the cells, the FITC fluorescence intensities from the cells treated with FITC-TAT, FITC-Spep001, FITC-Spep002 and FITC-Spep003 decreased.

According to the above result, it can be seen that the penetration of the cell-penetrating multifunctional peptide of the present disclosure into cells depends on energy.

<Example 9> Fabrication of Difunctional Peptide

A peptide effective in cell penetrability and skin improvement was fabricated. Specifically, KTTKS (SEQ ID NO: 5), Spep001-KTTKS (SEQ ID NO: 6), KTTKS-Spep001 (SEQ ID NO: 7) and palmitoyl-KTTKS peptides listed below in Table 5 were fabricated by SPPS.

TABLE 5

| CPPs | Sequence | MW | Purity |
|---|---|---|---|
| KTTKS (SEQ ID NO: 5) | KTTKS | 564.53 | 99.00% |
| Spep001-KTTKS (SEQ ID NO: 6) | RLRLRQRRRKTTKS | 2012.17 | 96.31% |
| KTTKS-Spep001 (SEQ ID NO: 7) | KTTKSRLRLRQRRRR | 2012.17 | 95.83% |
| Palmitoyl-KTTKS | Pal-KTTKS | 802.07 | 97.60% |

<Example 10> Cytotoxicity Assay of Difunctional Peptide

Figure 8A:
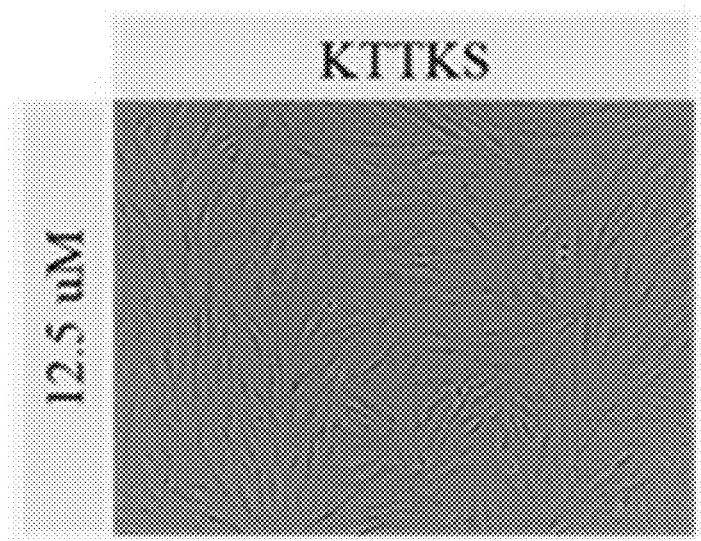
Figure 8A:
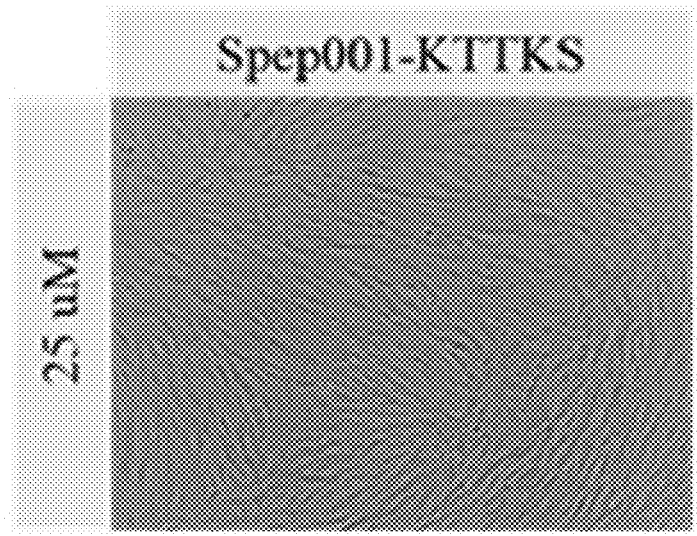
Figure 8A:
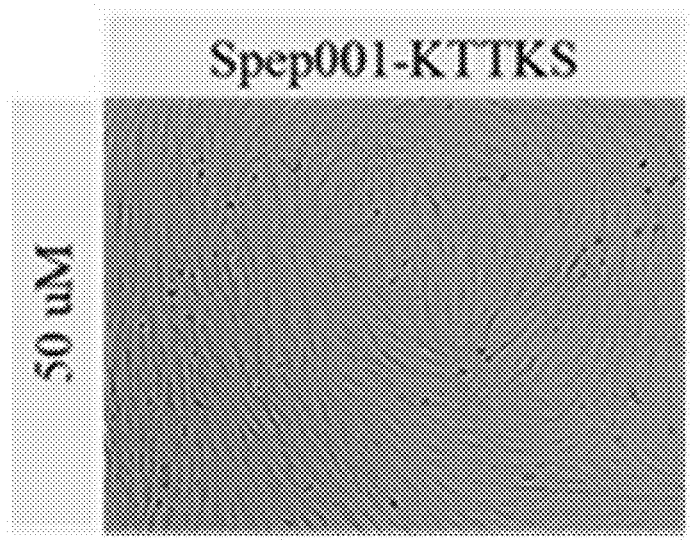

Cytotoxicity of the difunctional peptide fabricated in Example 9 was checked as in Example 3, and the result thereof is shown in FIG. 8A(i) to FIG. 8A(xii), FIG. 8B and Table 6 below. However, the difunctional peptide was treated with concentrations of 0 μM, 12.5 μM, 25 μM, 50 μM and 100 μM.

TABLE 6

| | HDF-N | | | | |
|---|---|---|---|---|---|
| | Peptide Concentration (μM) | | | | |
| Treatment | 0 | 12.5 | 25 | 50 | 100 |
| KTTKS (SEQ ID NO: 5) | 100.00 ± 10.11 | 103.93 ± 13.02 | 106.60 ± 20.09 | 105.23 ± 4.28 | 118.70 ± 11.56 |
| KTTKS-Spep001 (SEQ ID NO: 7) | 100.00 ± 10.11 | 110.7 ± 8.60 | 119.74 ± 4.46 | 107.25 ± 7.61 | 94.10 ± 3.20 |
| Spep001-KTTKS (SEQ ID NO: 6) | 100.00 ± 10.11 | 167.45 ± 13.38 | 147.73 ± 8.42 | 103.54 ± 3.16 | 105.82 ± 11.37 |

Referring to the images of the appearance of the cells shown in FIG. 8A(i) to FIG. 8A(xii), there was no change in the appearance of the cells treated with KTTKS (SEQ ID NO: 5), Spep001-KTTKS (SEQ ID NO: 6) and KTTKS-Spep001 (SEQ ID NO: 7) from a low concentration (12.5 μM) to a high concentration (100 μM).

Referring to the cell proliferation rates shown in FIG. 8B and Table 6 below, the cell proliferation rate of KTTKS-Spep001 (SEQ ID NO: 7) was maintained at a level similar to that of a control (0 μM). Further, it was confirmed that Spep001-KTTKS (SEQ ID NO: 6) remarkably increased the cell survival rate at a low concentration (12.5 μM) to 167.45±13.38%.

According to the above results, it can be seen that the difunctional peptide according to the present disclosure has no cytotoxicity and Spep001-KTTKS (SEQ ID NO: 6) remarkably increases cell proliferation.

<Example 11> Cell Proliferation Effect of Difunctional Peptide

HDF-N cells were treated with 12.5 μM KTTKS (SEQ ID NO: 5), Spep001-KTTKS (SEQ ID NO: 6) and pal-KTTKS which are peptides fabricated in Example 9. The appearance and proliferation rate of the cells were measured as in Example 3, and the results thereof are shown in FIG. 9A(i) to FIG. 9A(iv), FIG. 9B and Table 7 below.

TABLE 7

| Peptide | Cell viability(%) |
| --- | --- |
| Control | 100.00 ± 6.58 |
| KTTKS (SEQ ID NO: 5) | 110.58 ± 8.69 |
| Spep001-KTTKS (SEQ ID NO: 6) | 215.58 ± 2.14 |
| Palmitoyl-KTTKS | 109.22 ± 14.64 |

Figure 9A:
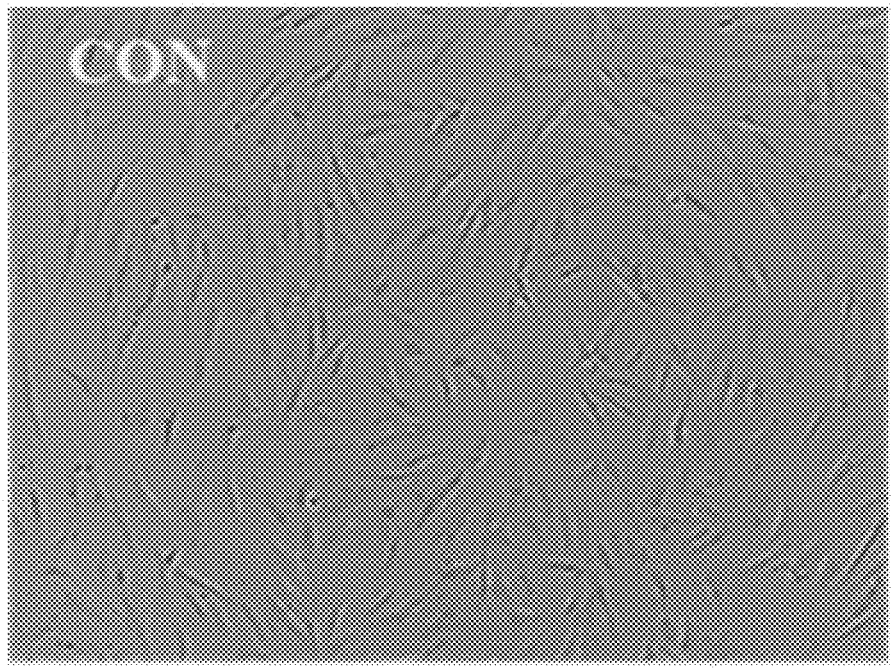
FIG. 9A(i) to FIG. 9A(iv) and FIG. 9B show microscopic images of the appearance of HDF-N cells treated with PBS(control), KTTKS (SEQ ID NO: 5), Spep001-KTTKS (SEQ ID NO: 6) or pal-KTTKS (FIG. 9A(i) to FIG. 9A(iv)) and also shows the result of checking the cell proliferation rate by a WST-1 assay (FIG. 9B) according to an example of the present disclosure.
Figure 9A:
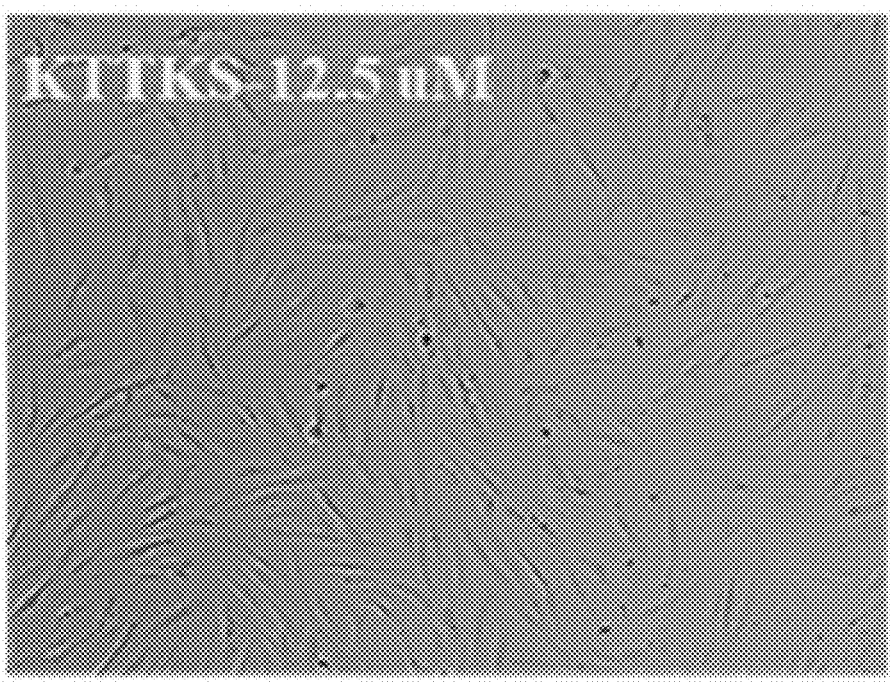

Referring to the images of the appearance of the cells shown in FIG. 9A(i) to FIG. 9A(iv), it was confirmed that there was no change in the appearance of the cells treated with KTTKS (SEQ ID NO: 5) and SPEP001-KTTKS (SEQ ID NO: 6), but the appearance of the cells treated with Pal-KTTKS was changed.

Figure 9B:
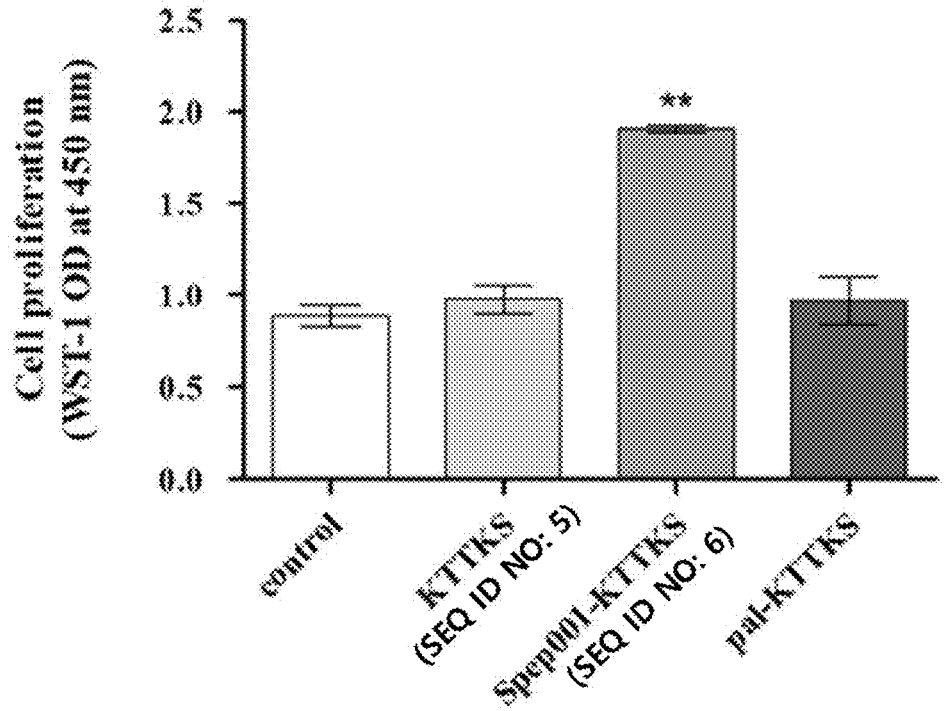

Also, referring to the cell proliferation rates shown in FIG. 9B and Table 7 below, Spep001-KTTKS (SEQ ID NO: 6) (215.58%) remarkably increased the cell growth rate by about two times compared to a control KTTKS (SEQ ID NO: 5) (110.58%) and pal-KTTKS (109.22%).

<Example 12> Evaluation on Synthesis of Collagen by Difunctional Peptide

HDF-N cells were inoculated at a concentration of 1×10⁴ cells/well into a 96-well plate and incubated for 24 hours. Then, the medium was removed, followed by washing twice with PBS, and replaced with a serum-free medium. Thereafter, 12.5 μM KTTKS (SEQ ID NO: 5), Spep001-KTTKS (SEQ ID NO: 6) and pal-KTTKS were added to each well and then incubated for 24 hours. Then, 10 μL of the cell culture fluid was obtained and centrifuged at 800 rpm for 5 minutes. Thereafter, the degree of synthesis of collagen was checked using a PIP (procollagen Type 1C-peptide) ELISA kit (MK101, Takara), and the result thereof is shown in FIG. 10 and Table 8 below.

TABLE 8

| Peptide | PIP(ng/ml) |
| --- | --- |
| Control | 127.03 ± 24.43 |
| KTTKS (SEQ ID NO: 5) | 203.24 ± 10.74 |
| Spep001-KTTKS (SEQ ID NO: 6) | 436.32 ± 39.51 |
| Pal-KTTKS | 188.84 ± 31.44 |

Figure 10:
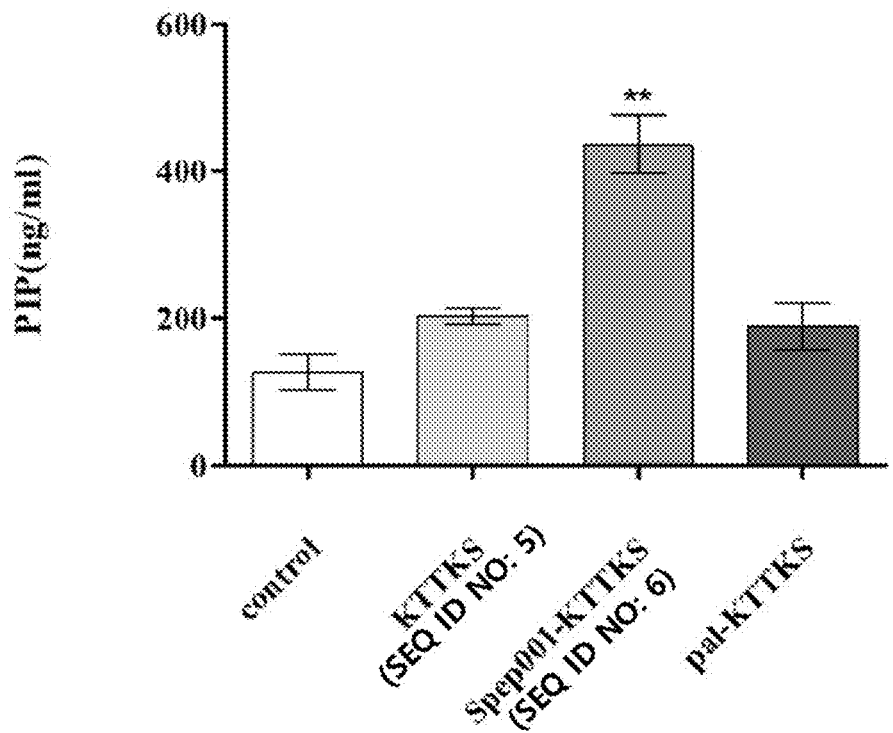
FIG. 10 shows the result of measuring the amount of collagen synthesized in a cell culture fluid by using a procollagen type I C peptide (PIP) ELISA kit after treating HDF-N cells treated with PBS (control), KTTKS (SEQ ID NO: 5), Spep001-KTTKS (SEQ ID NO: 6) or pal-KTTKS according to an example of the present disclosure.

Referring to the collagen synthesis concentration shown in FIG. 10 and Table 8, 127.03 ng/mL collagen was present in a control, 203.24 ng/mL collagen was present in KTTKS (SEQ ID NO: 5), 436.32 ng/mL collagen was present in Spep001-KTTKS (SEQ ID NO: 6), and 188.84 ng/ml collagen was present in pal-KTTKS.

According to the above result, it can be seen that the amount of collagen synthesized by Spep001-KTTKS (SEQ ID NO: 6) is remarkably greater by 343.47% than 159.99% for KTTKS (SEQ ID NO: 5) and 148.66% for pal-KTTKS based on the control.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

```
[sequence list]
SEQ ID NO: 1: Spep001
RLRLRQRRRR

SEQ ID NO: 2: Spep001
cgc ctg cgc ctg cgc cag cgc cgc cgc cgc

SEQ ID NO: 3: Spep001
cgg ctg cgg ctg cgg cag cgg cgg cgg cgg

SEQ ID NO: 4: Spep001
agg ctg agg ctg agg cag agg agg agg agg

SEQ ID NO: 5: Peptide
KTTKS

SEQ ID NO: 6: Spep001-KTTKS
RLRLRQRRRRKTTKS

SEQ ID NO: 7: KTTKS-Spep001
KTTKSRLRLRQRRRR

SEQ ID NO: 8: Spep002
KRRWRKIPKR

SEQ ID NO: 9: Spep003
RKRWLRKPRP

SEQ ID NO: 10: TAT
YGRKRRQRRR
```

We claim:

1. A cell-penetrating peptide, consisting of the amino acid sequence of SEQ ID NO: 1.

2. The peptide of claim 1,
wherein the cell-penetrating peptide is encoded with any one of nucleotides of SEQ ID NOs: 2 to 4.

3. A composition for drug delivery, comprising:
the cell-penetrating peptide according to claim 1; and
a target drug.

4. The composition of claim 3,
wherein the drug is a compound, a protein or a nucleic acid.

5. The composition of claim 4,
wherein the compound is at least one selected from the group consisting of fat, carbohydrate, dye, photosensitizer, anticancer drug, antibiotic and low-molecular compound.

6. The composition of claim 4,
wherein the protein is at least one selected from the group consisting of enzyme, ligand, hormone, carrier, immunoglobulin, antibody, structural protein, motor functioning peptide, receptor, signaling peptide, storing peptide, membrane peptide, transmembrane peptide, internal peptide, external peptide, secreting peptide, virus peptide, native peptide, glycated protein, fragmented protein, disulfide bonded protein, recombinant protein and chemically modified protein.

7. The composition of claim 4,
wherein the nucleic acid is at least one selected from the group consisting of coding nucleic acid sequence, mRNA, siRNA, microRNA, plasmid, gene, antisense RNA and oligonucleotide.

8. The composition of claim 4,
wherein the drug is linked to the N-terminus or C-terminus of the cell-penetrating peptide.

9. The composition of claim 4,
wherein the drug is linked to the cell-penetrating peptide through a linker.

10. A cosmetic composition for skin improvement, comprising:
the cell-penetrating peptide according to claim 1; and
a drug.

11. The composition of claim 10,
wherein the skin improvement is at least one selected from the group consisting of skin moisturizing, skin whitening, skin elasticity improvement, skin reproduction, and wrinkle improvement.

12. The composition of claim 10,
wherein the drug is a compound, a protein or a nucleic acid.

13. The composition of claim 10,
wherein the drug is a peptide consisting of the amino acid sequence of SEQ ID NO: 5.

14. The composition of claim 10,
wherein the drug is linked to the N-terminus or C-terminus of the cell-penetrating peptide.

\* \* \* \* \*